US012586690B2

(12) United States Patent
Larusson et al.

(10) Patent No.: US 12,586,690 B2
(45) Date of Patent: Mar. 24, 2026

(54) PLATFORM AND INTERFACES FOR FACILITATING COMMUNICATION IN A CLINICAL SERVICE ENVIRONMENT

(71) Applicant: ScribeAmerica, LLC, Fort Lauderdale, FL (US)

(72) Inventors: Fridrik Larusson, Seattle, WA (US); Vadim Vitalyevich Khazan, Seattle, WA (US); Paul Soto, Renton, WA (US); Amer Hukic, Sarajevo (BA); Timothy Aaron Grey, Nashville, TN (US); Ivan Yurov, Seattle, WA (US)

(73) Assignee: ScribeAmerica, LLC, Fort Lauderdale, FL (US)

(*) Notice: Subject to any disclaimer, the term of this patent is extended or adjusted under 35 U.S.C. 154(b) by 165 days.

(21) Appl. No.: 18/179,147

(22) Filed: Mar. 6, 2023

(65) Prior Publication Data

US 2024/0304339 A1    Sep. 12, 2024

(51) Int. Cl.
| | |
|---|---|
| *G06F 17/00* | (2019.01) |
| *G16H 15/00* | (2018.01) |
| *G16H 80/00* | (2018.01) |
| *H04L 51/216* | (2022.01) |
| *H04L 51/23* | (2022.01) |

(52) U.S. Cl.
CPC ............. *G16H 80/00* (2018.01); *G16H 15/00* (2018.01); *H04L 51/216* (2022.05); *H04L 51/23* (2022.05)

(58) Field of Classification Search
CPC ........ G16H 80/00; G16H 15/00; G16H 10/60; G16H 40/20; H04L 51/216; H04L 51/23
See application file for complete search history.

(56) References Cited

U.S. PATENT DOCUMENTS

| | | | | |
|---|---|---|---|---|
| 2009/0234675 A1* | 9/2009 | Irakam | ................... | G16H 40/63 |
| | | | | 705/2 |
| 2011/0046983 A1 | 2/2011 | Soble et al. | | |
| 2011/0093278 A1* | 4/2011 | Hutton | ................... | G16H 30/40 |
| | | | | 345/173 |
| 2012/0246715 A1 | 9/2012 | Toda | | |
| 2014/0156293 A1* | 6/2014 | Kozicki | ................. | G16H 40/67 |
| | | | | 705/2 |
| 2014/0222462 A1 | 8/2014 | Shakil et al. | | |
| 2015/0312533 A1 | 10/2015 | Moharir | | |
| 2017/0116384 A1* | 4/2017 | Ghani | ..................... | G16H 70/20 |
| 2017/0357453 A1* | 12/2017 | Ko | ......................... | G06F 3/0608 |
| 2018/0166081 A1 | 6/2018 | Koll et al. | | |

(Continued)

FOREIGN PATENT DOCUMENTS

| | | |
|---|---|---|
| WO | WO 2003/085577 | 10/2003 |
| WO | WO 2019/078887 | 4/2019 |
| WO | WO 2022/072346 | 4/2022 |

OTHER PUBLICATIONS

International Search Report and Written Opinion in International Appln. No. PCT/US2023/016758, mailed on Jul. 10, 2023, 10 pages.

(Continued)

*Primary Examiner* — Greta L Robinson
(74) *Attorney, Agent, or Firm* — Fish & Richardson P.C.

(57) ABSTRACT

Some implementations of a computer system or a computer-implemented method facilitate communication in a clinical services environment in which clinical notes or other portions of electronic health records that summarize a session between a patient and a health care provide are generated.

20 Claims, 22 Drawing Sheets

(56)          References Cited

U.S. PATENT DOCUMENTS

| | | | |
|---|---|---|---|
| 2018/0240538 A1 | 8/2018 | Koll et al. | |
| 2018/0324132 A1 | 11/2018 | Barnard et al. | |
| 2019/0035503 A1* | 1/2019 | Gonzalez | G16H 10/60 |
| 2019/0057760 A1 | 2/2019 | Schwartz et al. | |
| 2019/0272147 A1 | 9/2019 | Vozila et al. | |
| 2019/0272896 A1 | 9/2019 | Vozila et al. | |
| 2019/0304589 A1* | 10/2019 | Ishikawa | G16H 30/20 |
| 2020/0126643 A1 | 4/2020 | D'Souza et al. | |
| 2020/0168303 A1 | 5/2020 | Cane et al. | |
| 2021/0398630 A1 | 12/2021 | Sadeghi et al. | |
| 2023/0317225 A1 | 10/2023 | Larusson et al. | |
| 2024/0047049 A1 | 2/2024 | Larusson et al. | |

OTHER PUBLICATIONS

International Search Report and Written Opinion in International Appln. No. PCT/US2023/029117, mailed on Dec. 13, 2023, 19 pages.
International Search Report and Written Opinion in International Appln. No. PCT/US2024/018350, mailed on Jun. 24, 2024, 9 pages.
International Preliminary Report on Patentability in International Appln. No. PCT/US2024/018350, mailed on Sep. 18, 2025, 7 pages.

\* cited by examiner

Encounters  Schedules  *Projects*  Providers  Scribes  Training  Help

Q Search

New Project

| Project | Providers | Scribes | Encounters (24 hrs) | Due (4 hrs) | Overdue |
|---|---|---|---|---|---|
| Project A | _View_ | 4 | 8 | 45 | 12 | 2 |
| Project B | _View_ | 9 | 22 | 95 | 23 | 3 |
| Project C | _View_ | 2 | 5 | 18 | 4 | 0 |

300

Project A

← Feb. 3 – Feb. 9, 2022 →

■ Completed On Time  □ Completed Overdue

| THU 2/3 | FRI 2/4 | SAT 2/5 | SUN 2/6 | MON 2/7 | TUE 2/8 | WED 2/9 |

45 Encounters Received

2 Encounters Overdue

3 min, 35 sec Audio Length / Encounter

55 min Median Assigned to Completed

| Project ID | Identity Provider | ERH | Division | Billing Type | Region | Specialty |

🔍 Search

| Scribes | Providers |

| Name | Scheduled | Available | Due (4hrs) | Overdue |
| --- | --- | --- | --- | --- |
| Provider A1 View Profile | 12 | 3 | 2 | 1 |
| Provider A2 View Profile | 8 | 3 | 1 | 0 |
| Provider A3 View Profile | 11 | 2 | 2 | 0 |
| Provider A4 View Profile | 10 | 1 | 0 | 0 |

( Add Provider )

← Providers

Provider A1

| 1 Overdue | 0 STAT | 3 Available |
|---|---|---|

Today's Snapshot

Encounters Scheduled 12     Due (4hrs) 2

Project: Project A

Time Zone: America/Los Angeles

SLA: 24

Transcribe Audio:

History of present illness

Separate each medical problem reviewed into its own paragraph.

Allergies/meds/histories

Nurses will update this during intake, pull in from Nurse's notes.

Assessment and plan

If dictating, may occasionally state A&P info while dictating the HPI.

Review of systems

Templates:
Full Adult – Default for patients 18 years or older.
Full Child – Default for patients under age 18.

Physical exam

Annual Medicare – If EHR indicates patient is being seen for annual Medicare evaluation, use this template.

Templates

Encounters   *Schedules*   Projects   Providers   Scribes   Training   Help

Provider A1

| | 10 THU Feb | 11 FRI Feb | 12 SAT Feb | 13 SUN Feb |
|---|---|---|---|---|
| | Yesterday | Today | Tomorrow | Tomorrow +1 |
| 4:30 PM | | | | |
| 5:00 PM | | | | |
| 5:30 PM | | Add Encounter (5:15 PM) | | |
| 6:00 PM | | | | |
| 6:30 PM | | | | |
| 7:00 PM | | | | |

Add Encounter

*380*

Figure 4D:
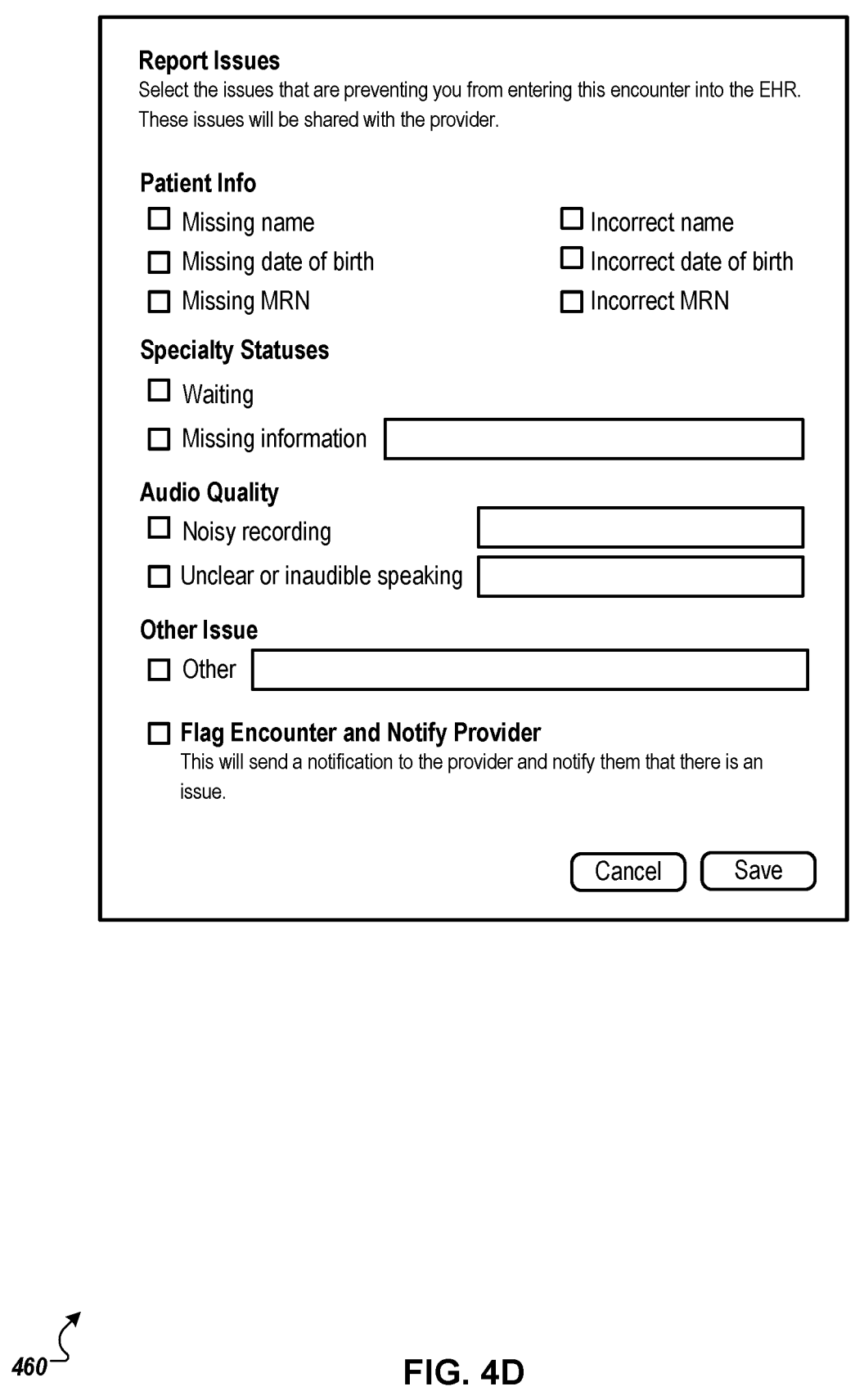

Report Issues

Select the issues that are preventing you from entering this encounter into the EHR. These issues will be shared with the provider.

Patient Info

☐ Missing name            ☐ Incorrect name

☐ Missing date of birth      ☐ Incorrect date of birth

☐ Missing MRN            ☐ Incorrect MRN

Specialty Statuses

☐ Waiting

☐ Missing information   [_____]

Audio Quality

☐ Noisy recording       [_____]

☐ Unclear or inaudible speaking   [_____]

Other Issue

☐ Other   [_____]

☐ Flag Encounter and Notify Provider
    This will send a notification to the provider and notify them that there is an issue.

( Cancel )    ( Save )

Receive Chat Message
*572a*

Determine Semantic Meaning
of Chat Message
*572b*

Is Chat Message
Mapped to Automated
Task?
*572c*

Determine Recipients
and Transmit Chat Message
*572f*

Transmit Automated Response
to Sender of Chat Message
*572d*

Perform Automated Task
*572e*

*572*

1

PLATFORM AND INTERFACES FOR FACILITATING COMMUNICATION IN A CLINICAL SERVICE ENVIRONMENT

TECHNICAL FIELD

This specification generally relates to a platform and interfaces for facilitating communication in a clinical service environment, such as an environment in which clinical notes or other portions of electronic health records that summarize a session between a patient and a health care provider are generated.

BACKGROUND

When conducting a session with a patient, a health care provider typically asks the patient various questions in order to understand the patient's condition for purposes of achieving a diagnosis or improved outcome. For example, the health care provider can inquire about the patient's medical history, the nature of current symptoms the patient is experiencing, medications currently being taken by the patient, and so forth. After examining the patient and arriving at a diagnosis, the health care provider can formulate a plan for treating the patient, which may include various therapies and medical prescriptions. A clinical note that documents the session, including the patient's feedback to the questions and, optionally, the diagnosis and treatment plan, can be generated for storage by an electronic health record (EHR) system. Sometimes, medical scribes are employed to assist the health care provider with preparing and submitting the clinical note.

SUMMARY

This document generally describes computer systems, processes, program products, and devices for facilitating the generation of clinical notes or other portions of electronic health records that summarize a session between a patient and a health care provider, and for facilitating communication in a clinical service environment. Some implementations of the system described herein can provide an improved, simplified interface for a physician or other health care provider, can efficiently route session information to one or more remote medical scribes, and can provide an improved scribe interface that enhances each scribe's capability to rapidly filter and accurately summarize the session information to generate clinical notes for importation into the healthcare provider's electronic health record (EHR) system. In some embodiments, an onboarding process can be conducted with a health care provider, during which various preferences of the health care provider are collected and recorded (e.g., an electronic health record (EHR) system used by the provider, templates used by the provider, and other relevant preferences). The health care provider can conduct a health care session with a patient, during which the health care provider and the patient discuss various topics. Based on the discussion and on the health care provider's observations, the health care provider can diagnose the patient and can determine an appropriate treatment plan. The health care provider can use a portable computer device (e.g., carried during the session with the patient) to upload a recording (e.g., audio recording or audio-visual recording) of the session to a server system, along with other session information. The server system can process the recording, and can provide the processed recording, a transcription of the recording, the session information (e.g., information that specifically pertains to the particular health care session between the health care provider and the patient), and additional metadata that is associated with the health care provider and is not specific to the particular health care session, to a remote computing device operated by an authorized medical scribe for purpose of generating a clinical note for the session. After the clinical note has been generated by the scribe, the scribe interface at the remote computing device can be used to upload the clinical note to an EHR system, the health care provider can receive a notification that the clinical note is complete and, optionally, can be prompted to review and approve the clinical note generated by the remote scribe.

In some implementations, a method may be performed by data processing apparatuses. The method includes receiving, by a practitioner interface device, a command to record media data that pertains to a health care session that has been conducted between a health care provider and a patient; transmitting the media data, by the practitioner interface device and to a server system; receiving, by the practitioner interface device and from the server system, a media data receipt notification that indicates that the server system has received the media data; in response to receiving the media data receipt notification, removing the media data from the practitioner interface device; after removing the media data from the practitioner interface device, receiving, by the practitioner interface device and from the server system, a task completion notification that indicates that a task that pertains to the health care session and the media data has been completed; after receiving the task completion notification, updating a practitioner interface of the practitioner interface device to present one or more feedback controls for the completed task; and providing, by the practitioner interface device and to the server system, feedback data for the completed task, based on input that has been received through the one or more feedback controls presented by the practitioner interface.

Other implementations of these aspect include corresponding computer systems, and include corresponding apparatus and computer programs recorded on one or more computer storage devices, each configured to perform the actions of the methods. A system of one or more computers can be configured to perform particular operations or actions by virtue of having software, firmware, hardware, or a combination of them installed on the system that in operation causes or cause the system to perform the actions. One or more computer programs can be configured to perform particular operations or actions by virtue of including instructions that, when executed by data processing apparatus, cause the apparatus to perform the actions.

These and other implementations may optionally include any or all of the following features. The practitioner interface can include a plurality of selectable task controls. Each selectable task control can represent a different task to be performed for the health care provider and can include a task status indicator that provides a visual indication of a current status of the task. In response to receiving the media data receipt notification, the task status indicator of the selectable task control that represents the task that pertains to the health care session can be updated to indicate that the media data has been uploaded. After receiving the media data receipt notification and before receiving the task completion notification, a process notification can be received by the practitioner interface device and from the server system. The process notification can indicate that a remote scribe device is currently processing the task. In response to receiving the process notification, the task status indicator of the selectable task control that represents the task that pertains to the health care session can be updated to indicate that the task is currently being processed by the remote scribe device. In response to receiving the task completion notification, the task status indicator of the selectable task control that represents the task that pertains to the health care session can be updated to indicate that the task has been completed. Updating the practitioner interface of the practitioner interface device to present one or more feedback controls for the completed task can be performed in response to receiving a selection of the selectable task control that represents the completed task that pertains to the health care session. After receiving the media data receipt notification and before receiving the task completion notification, an interference issue notification can be received by the practitioner interface device and from the server system. The interference issue notification can indicate that a remote scribe device that is processing the task has flagged an interference issue that indicates a defect with the media data. In response to receiving the interference issue notification, the task status indicator of the selectable task control that represents the task that pertains to the health care session can be updated to indicate that the interference issue exists for the task. A selection of the selectable task control that represents the task that pertains to the health care session, and for which the interference issue exists, can be received. In response to receiving the selection of the selectable task control, the practitioner interface of the practitioner interface device can be updated to present one or more controls for providing additional task data for correcting the interference issue. The additional task data can be provided, by the practitioner interface device and to the server system, based on input that has been received through the one or more controls for providing the additional task data. In response to a selection of a chat control of the practitioner interface of the practitioner interface device, the practitioner interface can be updated to present a plurality of selectable chat thread controls. Each selectable chat thread control can represent an ongoing chat thread between the practitioner interface device and one or more remote scribe devices. At least one of the selectable chat thread controls can represent the ongoing chat thread between the practitioner interface device and a remote scribe device that is processing the task that pertains to the health care session and the media data.

The systems, devices, program products, and processes described throughout this document can, in some instances, provide one or more of the following advantages. First, particular implementations of the system can employ a practitioner interface device that, in response to a health care provider ending a session recording, automatically begins transferring an audio file to a system server using resumable upload techniques. As such, the file transfer can resume from a last point of transfer (rather that from the beginning) if a transfer is interrupted at any point due to a poor network connection. Second, in some implementations, after an audio file has been successfully uploaded, the uploaded file can be deleted from local storage of the practitioner interface device, thus freeing up storage resources and maintaining the security of patient data. Third, in particular implementations, by trimming and noise filtering uploaded audio files, downstream processes can be more efficiently and accurately performed, and data storage can be conserved. Fourth, in some implementations, audio files related to health care sessions can be automatically routed to skill-matched medical scribes that can complete clinical notes for the health care sessions in a timely manner. The automatic, computer selection of skill-matched tasks for medical scribes can be efficiently solved through interactions between platform devices, and through the maintenance and use of task complexity scores and scribe quality scores. Fifth, in some implementations, a health care provider can receive, through an application interface presented by the practitioner interface device, timely notifications of issues with the audio files (or related metadata) that would interfere with the generation of a clinical note. Sixth, in some implementations, a clinical note generation interface can include multiple related portions serving different functions, with one portion of the interface being used by a medical scribe for working on a clinical note, and easy reference to source information and instructions for generating the note being provided through other portions of the interface. Additionally, automatically highlighting key terms in a transcript and/or pre-populating a note generation working area (e.g., based on automatically selected note templates and relevant clinical information) can facilitate quick identification of relevant portions of a transcript and generation of a clinical note. Seventh, some implementations of the system can be used to map a transcript to a media file so as to facilitate reviewing and verifying the transcript. Eighth, in some implementations, medical scribes can generate clinical notes for health care sessions independent of health care providers, such that downtime of the medical scribes is minimized. Ninth, in some implementations, clinical notes (which may be generated by a medical scribe remote from a heath care provider) can be automatically input into the health care provider's electronic health record (EHR) system. Tenth, in particular implementations, a mechanism can be included for health care providers to easily provide feedback for specific tasks through the clinical data platform, such that the feedback can be provided without directly including specific patient information, thus ensuring patient data privacy. As detailed more below, multiple ongoing communications can be effectively managed through integrated interfaces.

Some implementations described herein include a session recording that is stored and transferred as an audio file, but it should be also understood from the detailed teaching herein that the audio file can include audio data only, both audio data and video data, or other combinations of audio data and other information. In such cases, the system can use the file to generate a transcript from the session recording. Other features, aspects and potential advantages will be apparent from the accompanying description and figures.

DESCRIPTION OF DRAWINGS

FIGS. 3A-E depict example interfaces for onboarding health care providers and medical scribes onto a platform for facilitating the generation of clinical notes.

FIGS. 4A-G depict example interfaces for facilitating the generation of clinical notes.

Like reference symbols in the various drawings indicate like elements.

DETAILED DESCRIPTION

This document describes technology that can facilitate the routing of clinical data, such as clinical notes or other portions of electronic health records that summarize a session between a patient and a health care provider. In general, a health care provider (e.g., a physician, a nurse, or other practitioner who performs medical services for a patient) can conduct a health care session with a patient, during which the health care provider and the patient share information regarding pertinent health information, such as the patient's medical history, current symptoms, current medications, etc. Based on the discussion and on the health care provider's observations, the health care provider can diagnose the patient and can determine an appropriate treatment plan for the patient, which can include various therapies and/or medical prescriptions. Using a stationary or mobile computing device of the health care provider (sometimes referred to as a "practitioner interface device"), the health care provider can record (as audio data, both audio and video data, or audio data in combination with other recorded information) some or all of the session with the patient, and can upload the recording to a server system. As detailed below, the server system can perform various processing operations on the recording, and can provide the recording, a transcription of the recording, and related metadata to a client device operated by a suitable remote medical scribe (e.g., a professional who is trained on reviewing session recordings and generating a clinical note for a health care session, according to a format designated by a health care provider and/or an electronic health record (EHR) system used by the health care provider). After the clinical note has been entered into the EHR system, the health care provider can be notified by the server system (e.g., through the practitioner interface device or another device), and the health care provider can review and approve the clinical note. Some implementations of the platform described herein can more rapidly distribute session recordings to an authorized set of remote medical scribes that are equipped with an improved scribe interface at their respective computing device, thereby facilitating an efficient and accurate generation of clinical notes while allowing health care providers to spend more time treating patients and less time generating documentation. Further, an integrated system in which inter-application communication is handled as part of a workflow can maintain data security while maintaining high standards for work product.

Figure 1:
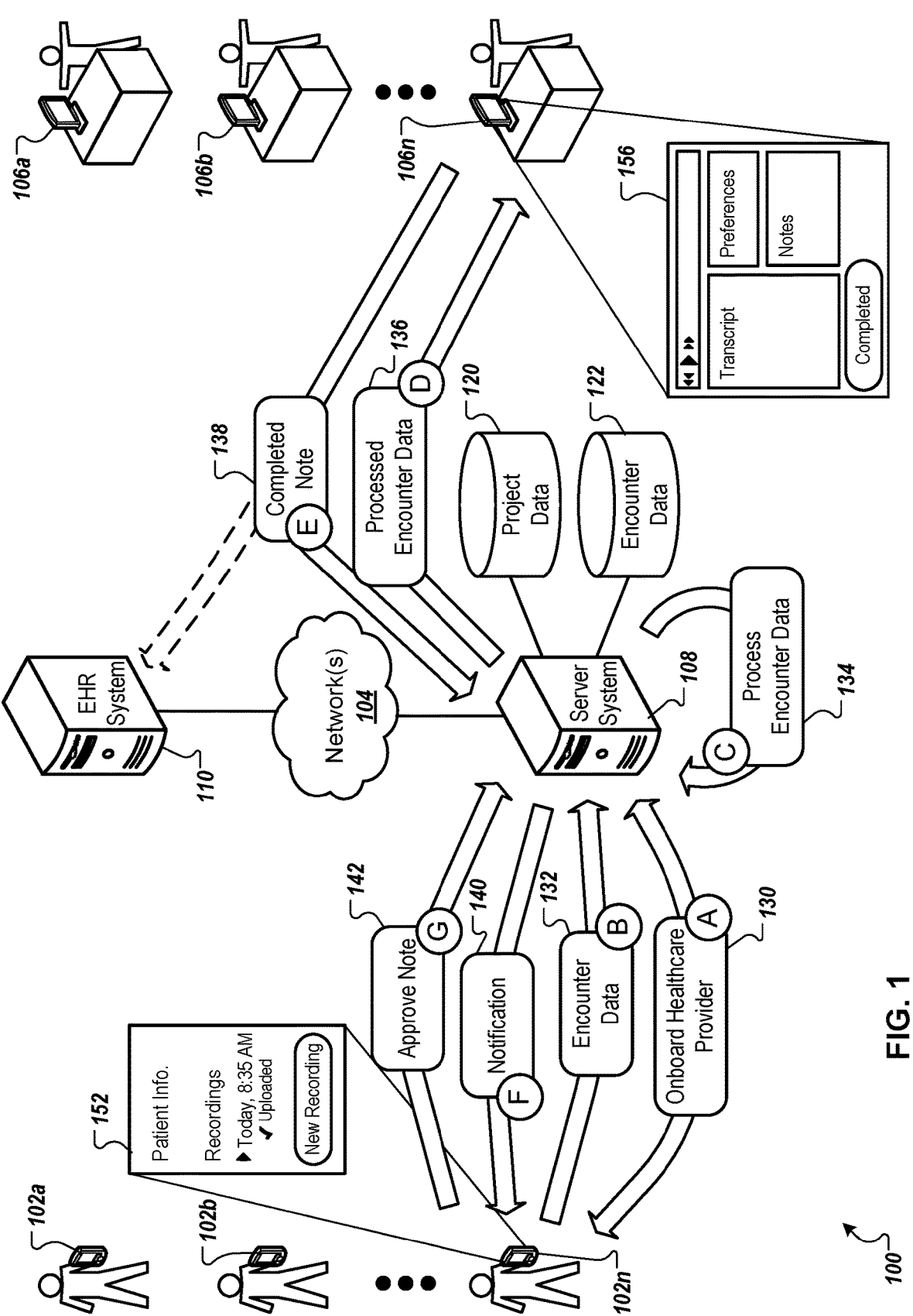
FIG. 1 is a diagram of an example system for facilitating the generation of clinical notes, in accordance with some embodiments.

FIG. 1 is a diagram of an example system 100 for facilitating the generation of clinical notes, as represented in example stages (A) to (G). Stages (A) to (G), for example, may occur in the illustrated sequence, a different sequence, and/or two or more stages (A) to (G) may be concurrent. In some examples, one or more stages (A) to (G) may be repeated multiple times when generating a clinical note.

In the present example, the system 100 includes multiple different mobile devices (e.g., practitioner interface devices 102a-n), each mobile device being operated by a respective health care provider. The practitioner interface devices 102a-n, for example, can include personal computers, laptop computers, smartphones, digital assistants, tablets, or other sorts of stationary or mobile computing devices that are configured to receive input from an operator (e.g., tactile input received through a controls presented on a touch screen and/or physical device controls, spoken input received through a microphone, activation commands received from a remote control device (such as a Bluetooth device), etc.), to present output to the operator (e.g., tactile, audio, and/or visual interfaces and notifications), to record a health care session conducted by the operator (e.g., with the recording including audio data, both audio data and video data, or other combinations of audio data and other information), and to communicate with other system components over communications network(s) 104. The system 100 in the present example also includes multiple different client devices (e.g., remote scribe devices 106a-n), each client device being operated by a respective medical scribe. The remote scribe devices 106a-n, for example, can include various mobile or stationary computing devices including, but not limited to a desktop computer, a laptop computer, a tablet computer, a digital assistant, a smartphone, or other suitable computing devices. Similar to the practitioner interface devices 102a-n, for example, the remote scribe devices 106a-n can be configured to receive input from an operator, to present output to the operator, and to communicate with other system components over communication network(s) 104. The communication network(s) 104, for example, can include one or more of a LAN (local area network), a WAN (wide area network), and/or the Internet.

The practitioner interface devices 102a-n and the remote scribe devices 106a-n in the present example can each communicate over network(s) 104 (e.g., sending data to and/or receiving data from) with a server system 108 and an electronic health record (EHR) system 110. Each of the server system 108 and the EHR system 110, for example, can include one or more computing servers (e.g., application servers, data servers, cloud servers, etc.). The server system 108, for example, can serve as an intermediary device between the practitioner interface devices 102a-n, the remote scribe devices 106a-n, and optionally, the EHR system 110. In some implementations, an application programming interface (API) of the server system 108 can use web sockets to send data to and receive data from the practitioner interface devices 102a-n and the remote scribe devices 106a-n in real time. For example, many features of the API can be shared by practitioner interface applications running on the practitioner interface devices 102a-n and by remote scribe interface applications running on the remote scribe devices 106a-n.

In the present example, the server system 108 can include and/or communicate with a project data store 120 and an encounter data store 122. Each of the data stores 120, 122, for example, can include data servers, file systems, and/or other suitable types of data storage devices or systems. The project data store 120, for example, can receive, store, and provide data related to the practitioner interface devices 102a-n and their respective operators (e.g., health care providers), data related to the remote scribe devices 106a-n and their respective operators (e.g., medical scribes), and organizational relationships between the health care providers and medical scribes. The encounter data store 122, for example, can receive, store, and provide data related to health care sessions (e.g., visits, encounters, etc.) between the health care providers and patients of the health care providers. Although a single EHR system (e.g., EHR system 110) is shown in the present example, in other examples, the server system 108 (and optionally, the practitioner interface devices 102a-n and the remote scribe devices 106a-n) can each communicate with multiple different EHR systems. For example, some health care providers may use different EHR systems than other health care providers.

During stage (A), an onboarding process 130 can occur, during which an account can be created for a health care provider on the server system 108, and the health care provider can receive login information and/or an application for accessing the server system. When setting up the account, for example, the health care provider can contact a representative of a clinical note generation platform who assists the provider with gathering and entering details for the account, or the health care provider can directly interact with an interface of the platform for setting up the account. In general, various preferences of the health care provider are recorded (e.g., EHR used by the provider, templates used in the EHR, note generation preferences, and other relevant preferences), various medical scribes are trained and/or selected for possible pairing with the health care provider, and the health care provider receives a mechanism (e.g., an application, a web link, etc.) for accessing the platform on their practitioner interface device.

Referring now to FIGS. 3A-E, example interfaces are shown for onboarding health care providers and medical scribes onto a platform for facilitating the generation of clinical notes, and generally for providing data visibility and management functions. The example interfaces can be presented by an application (e.g., a web-based application and/or a locally executed application) provided by the server system 108. Example interface 300 (shown in FIG. 3A) shows a list of various projects that are maintained by the platform. In general, a project can represent a group of health care providers, and a group of medical scribes that have been approved for generating clinical notes for the group of health care providers. For example, a project can be associated with a medical facility (e.g., a hospital, a clinic, or another sort of medical facility) at which the group of health care providers conduct health care sessions with various patients, and with metadata such as an identifier of an electronic health record (EHR) system used by the health care providers, a billing model, a service level agreement, and other suitable metadata. In the present example, the interface 300 provides summary information for each project in the list of projects, including a number of health care providers that are associated with the project, a number of medical scribes that have been assigned to the project, a number of encounters (e.g., a health care session or visit between a health care provider and a patient) that have occurred over a specified time period (e.g., twenty-four hours, or another suitable time period), a number of encounters for which a clinical note is due within a specified time period (e.g., four hours, or another suitable time period), and a number of encounters for which a clinical note is overdue. In addition to using the interface 300 (and additional interfaces described in examples below) for onboarding health care providers and medical scribes to existing or newly created projects, the interfaces can be used for viewing statistics related to various projects and managing the projects.

To associate health care providers and medical scribes with a project, for example, a user can select a project from the list of projects (e.g., by interacting with a project view control), and in response can be presented with an interface that includes information related to the selected project. For example, interface 320 (shown in FIG. 3B) shows information associated with "Project A," including a project identifier, an identity provider for the project, an electronic health record (EHR) system for the project, a division for the project, a billing type for the project, a region for the project, and a specialty for the project. In the present example, the interface 320 can also present various statistics for the project, such as a number of encounters for which data has been received from health care providers associated with the project, a number of encounters that are overdue (e.g., a designated completion time for a clinical note generation task is before a present time), an average audio duration of data files for the encounters, and a median amount of time between a clinical note generation task for the encounter having been assigned to a medical scribe and a completion time for the clinical note. Some or all of the project statistics can be presented in a graphical format, such as a bar graph in which, for each day of a selected week, a number of clinical notes for encounters having been completed on time is represented by a first bar, and a number of clinical notes for encounters having been completed overdue is represented by a second bar. In the present example, a list of health care providers that are associated with "Project A" is presented (e.g., health care providers that belong to an organization represented by the project), along with various statistics for each provider, such as a number of scheduled encounters for the provider during the present workday, a number of clinical note generation tasks that are available to be assigned to a medical scribe, a number of clinical note generation tasks that are due in a specified period of time (e.g., four hours, or another suitable time period), and a number of clinical note generation tasks that are overdue.

When onboarding a health care provider onto the platform for facilitating the generation of clinical notes, for example, a user can select a control to add a provider, and in response can be presented with an interface for specifying various preferences of the provider. Similarly, a user can select a health care provider from the list of health care providers (shown in FIG. 3B), and in response can be presented with the interface for viewing provider statistics and/or editing provider preferences. For example, interface 340 (shown in FIG. 3C) shows information associated with "Provider A1," including a project with which the health care provider is associated, a time zone for the provider, a service level agreement (SLA) for the provider, and an indication of whether audio files associated for encounters of the provider are to be transcribed. In the present example, the interface 340 can also present various statistics for the provider, such as a number of clinical note generation tasks for the provider that are currently available for assignment, a number of clinical note generation tasks that are to be completed as soon as possible (e.g., the tasks have been marked as "STAT" by the provider), a number of clinical note generation tasks that are currently overdue, a number of encounters that have been scheduled for the current day, and a number of clinical note generation tasks that are due in a specified period of time (e.g., four hours, or another suitable time period). The interface 340 in the present example can also be used to enter or edit note generation preferences (e.g., verbose vs. succinct), quality tracking preferences, and/or template preferences of the provider for various portions of a clinical note, such as a history of present illness, a review of systems, allergies/medications/histories, a physical exam, an assessment and plan, and/or other portions of the clinical note.

A template preference, for example, can include specifying a named template of an electronic health record (EHR) system. A template, for example, can be a pre-filled (e.g., boilerplate) and pre-structured clinical note for the EHR, designed for a particular type of encounter (e.g., an annual medical exam, a review of systems for an adult, a review of systems for a child, etc.). For example, a particular EHR may have dozens or hundreds of available templates, whereas a health care provider may only use a small subset of the available templates. Template preferences of a health care provider can be stored, and later used for generating clinical notes for the provider. For example, one or more templates from the subset of available templates that are used by the health care provider can be automatically selected when a clinical note is to be generated, based on metadata associated with an encounter (e.g., scheduling information that indicates that an encounter is of a particular type). As another example, a medical scribe can manually select a template from the subset of available templates, based on information specified in a transcript of the encounter (e.g., a health care provider specifying that a particular template is to be used when generating a clinical note for the encounter).

Figure 3A:
Figure 3D:
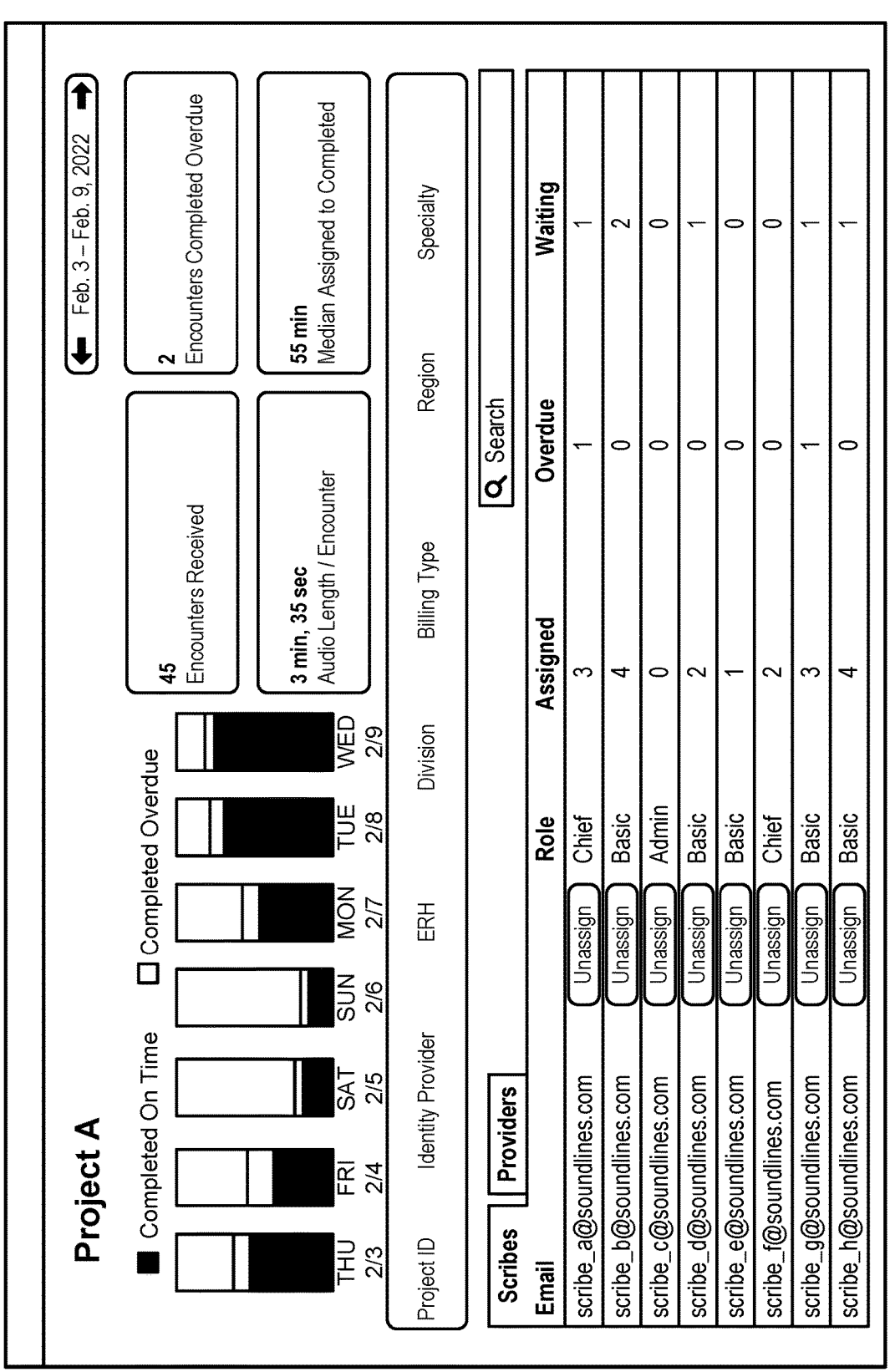

Referring to FIG. 3D, example interface 360 is shown for associating (and disassociating) medical scribes with a project. Similar to interface 320 (shown in FIG. 3B), for example, the interface 360 can present information and statistics related to a selected project. For example, a user can switch between views of a health care provider list for a project (interface 320, shown in FIG. 3B), and a medical scribe list for a project (interface 360, shown in FIG. 3D), by interacting with a control (e.g., a tab control or another suitable control) that facilitates switching between the lists. In the present example, a list of medical scribes that are associated with "Project A" is presented (e.g., medical scribes that have been approved to work on clinical notes for encounters of health care providers that are associated with the project), along with various statistics for each scribe, such as a role (e.g., chief or supervising, basic, administrator, or another sort of role), a number of clinical note generation tasks that are currently assigned to the scribe, a number of clinical note generation tasks that are currently overdue, and a number of clinical note generation tasks that are currently waiting (e.g., the scribe is waiting for additional encounter information from a health care provider before completing a note). In general, a medical scribe can be approved to work on clinical notes for various different projects (e.g., groups of health care providers), whereas a health care provider is generally associated with a single project.

Figure 3E:

Referring to FIG. 3E, example interface 380 is shown for maintaining a schedule of encounters for a health care provider. For example, a user can manually load a provider's schedule, including dates and times of planned sessions with various patients, in advance of the sessions occurring. As another example, the platform for facilitating the generation of clinical notes can be integrated with an electronic health record (EHR) system used by a provider, and the provider's schedule can be automatically be retrieved by the platform from the EHR system.

Referring again to FIG. 1, data collected during the onboarding process 130 can be stored by the server system 108 using the project data store 120. After the onboarding process 130 for a healthcare provider has occurred, for example, the provider can access the clinical note generation platform. In the present example, a health care provider can use practitioner interface device 102*n* to access an application (e.g., a native application, a web-based application, or another sort of application) that can receive schedule and patient information from the server system 108, and can present the information to the health care provider through a practitioner interface 152. For example, the health care provider can select a patient from a patient list presented by the practitioner interface 152 when conducting a health care session with the patient, and the practitioner interface 152 can present information related to the patent (e.g., patient name, patient identifier, date of birth, and other relevant information) to the provider. As another example, the health care provider can use the practitioner interface 152 to enter patient information. During and/or after conducting the session, for example, the health care provider can interact with the practitioner interface 152 to initiate the recording of one or more audio files that pertain to the session, on the practitioner interface device 102*n*. In some implementations, a practitioner interface used by a health care provider can include a control for indicating a type of task to be performed for an encounter. In general, a task can be an operation that is to be performed and completed, based on clinical data for a patient. For example, the type of task can be a generation of a clinical note to be uploaded to an electronic health record (EHR) system, an order of a medication and/or medical service (e.g., an x-ray, a blood sample, or another sort of service), a referral to be provided to another health care provider, or another sort of task.

During stage (B), encounter data 132 can be transferred from the practitioner interface device 102*n* to the server system 108. The encounter data 132, for example, can include the one or more audio files that pertain to the health care session conducted by the health care provider, and can include additional metadata related to the session (e.g., time of session, place of session, an indication of whether a clinical note for the encounter is to be generated without delay (STAT) or within a normal timeframe, etc.), and/or additional metadata related to the patient and/or the provider (e.g., names, identifiers, etc.). In some implementations, encounter data can be transferred from a practitioner interface device to a server system without receiving specific input from a health care provider to initiate the transfer. For example, after the health care provider ends a session recording, the practitioner interface device 102*n* can automatically begin transferring an audio file to the server system 108. Resumable upload techniques can be used to transfer the audio file, for example, such that a file transfer can resume from a last point of transfer (rather that from the beginning), if a transfer is interrupted at any point due to poor network connection. After the file has been received by the server system 108, for example, the server system can notify the practitioner interface device 102*n* that the file has been received. In response to the notification of successful upload, for example, the practitioner interface application can automatically delete the uploaded audio file from local storage of the practitioner interface device 102*n*, thus freeing up storage resources. If a healthcare provider later requests to review the audio file through the practitioner interface application, for example, the file can be streamed by the server system 108 to the practitioner interface device 102*n*.

Figure 2:
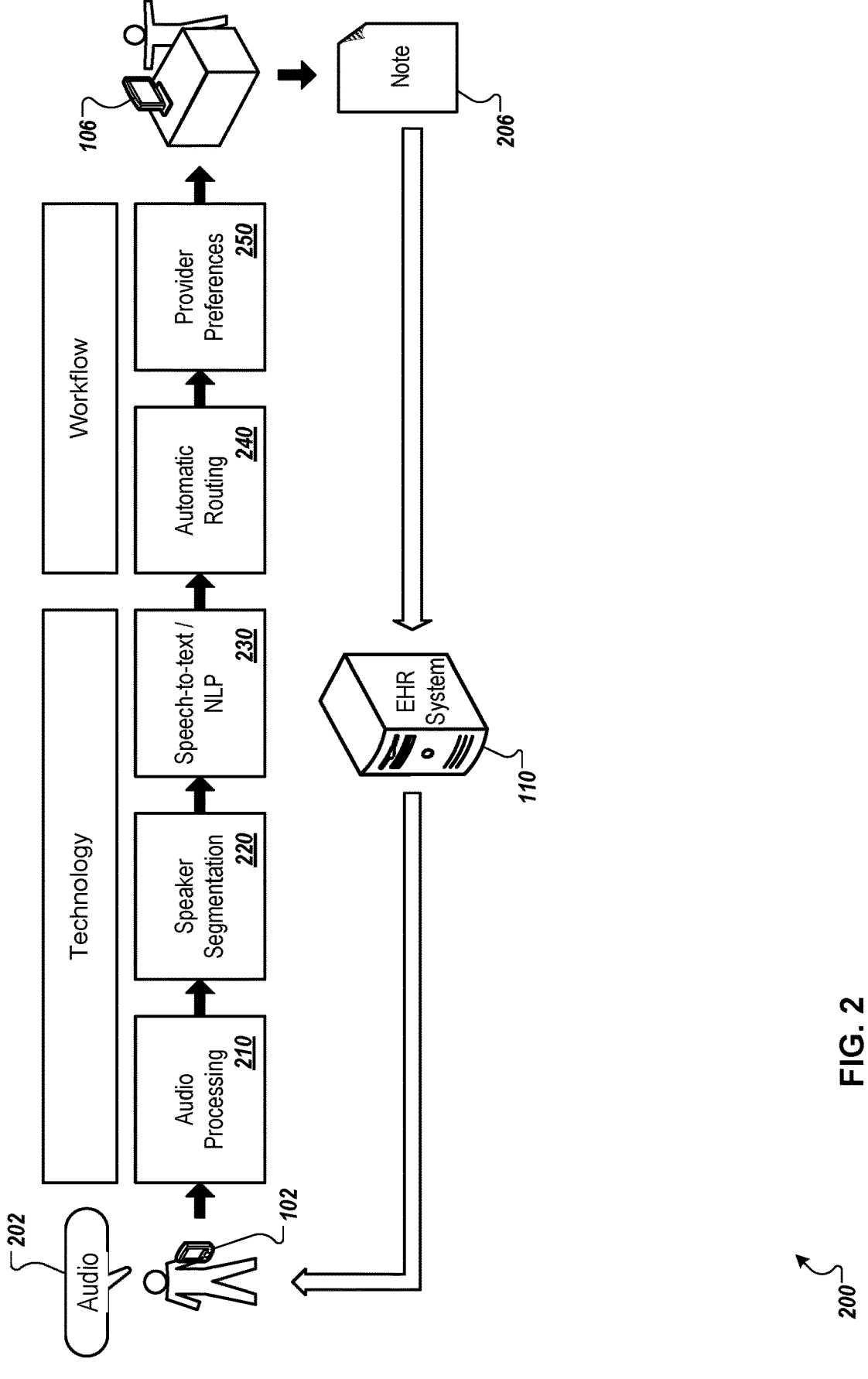
FIG. 2 is a diagram that illustrates example technology and workflow features for facilitating the generation of clinical notes.

During stage (C), a process 134 for processing the encounter data 132 can occur, during which various audio processing, speaker segmentation, and speech-to-text techniques can be performed on the one or more audio files included in the encounter data. Referring now to FIG. 2, for example, a diagram 200 illustrates example technology and workflow features for facilitating the generation of clinical notes. As shown in FIG. 2, for example, practitioner interface device 102 (e.g., any of practitioner interface devices 102*a-n*, shown in FIG. 1) can be used to record audio data 202 during or after a health care session between a health care provider and a patient (e.g., one or more audio files included in the encounter data 132, shown in FIG. 1). In some examples, the audio data 202 can be or can include a lossless, uncompressed audio file (e.g., 16,000 Hz), or another audio format that is suitable for speech-to-text operations.

The audio data 202 can be provided to an audio processing engine 210, which can perform basic checks to ensure that the audio data is correctly formatted and does not include computer viruses. After performing the basic checks, for example, the audio processing engine 210 can perform noise filtering and selective silence reduction on the audio data 202. A selective silence reduction operation, for example, can include detecting voice activity in the audio data (e.g., based on the frequency of human voices), and eliminating portions of the audio data in which speaking does not occur. A trimmed audio data can be run through a noise filtering operation to minimize background noise that may be present in the audio. By trimming and noise filtering the audio data 202, for example, downstream processes can be more efficiently and accurately performed (e.g., improving a word error rate in an automatically generated transcript), and data storage can be conserved.

Processed audio data 202 can be provided to a speaker segmentation engine 220, which can identify segments of the audio according to speaker. For example, the speaker segmentation engine 220 can provide the processed audio data 202 to a machine learning model that is trained to recognize segments of the audio that are spoken by a particular health care provider, and segments that are spoken by other individuals. Training the machine learning model to recognize audio segments of the particular health care provider, for example, can occur as part of an onboarding process for the health care provider. For example, audio data of the health care provider speaking can be collected during the onboarding process to acquire an acoustic model of the health care provider's voice, which can be used to improve the performance of the machine learning model during production. As another example, audio data of an initial encounter conducted by the health care provider can be manually segmented, labeled, and provided to the machine learning model for training, and processed audio data for subsequent encounters can be provided to the machine learning model for automatic segmentation.

The processed and segmented audio data 202 can be provided to a speech-to-text/natural language processing (NLP) engine 230, which can generate a transcript for the session between the health care provider and the patient, with each segment of spoken audio being labeled by speaker. After the session transcript has been generated, for example, natural language processing techniques can be used to identify, and to denote (e.g., mark, underline, highlight, etc.) key terms (e.g., medical terms, terms used in diagnoses, names of medications, and other key terms) that are present in the transcript. A generated transcript with denoted key terms can be presented in a note generation interface, for example, to facilitate clinical note generation tasks. Optionally, the generated transcript with identified key terms can be used to automatically populate at least a portion of an electronic health record (EHR) note. For example, key terms can be mapped to portions of a template for the EHR note, and a completed (or partially completed) note can be automatically prepared for review by a scribe and/or health care provider.

The audio processing engine 210, the speaker segmentation engine 220, and the speech-to-text/NLP engine 230, for example, can each include software and/or hardware components of the server system 108 (shown in FIG. 1). After the process 134 for processing the encounter data 132 is complete, for example, a priority level for generating a clinical note (and/or performing another sort of task for the encounter) for the encounter can be determined (e.g., based on a "STAT" indication by the health care provider, service agreements that are in place for the provider, and/or a type of task indicated by the health care provider), and metadata associated with the encounter data 132, the generated transcript, one or more audio files corresponding to the processed audio data 202 (and optionally, the original audio data) can be stored by the server system 108 using the encounter data store 122.

Referring again to FIG. 1, during stage (D), processed encounter data 136 can be provided to a suitable medical scribe. For example, the processed encounter data 136 (e.g., including associated metadata, one or more processed audio files, and a transcript based on the audio files) can be provided by the server system 108 to remote scribe device 106*n* of a respective medical scribe. In the present example, the processed audio file(s), the transcript, and preferences of the health care provider that submitted the encounter data 132 can be presented to the medical scribe through a remote scribe interface 156 (e.g., an application interface, a web-based interface, etc.) presented by remote scribe device 106*n*. Referring again to FIG. 2, for example, an automatic routing engine 240 can use various metadata to route notifications of available encounters (and optionally, to automatically assign tasks for encounters) to medical scribes that have been approved to work on tasks for the available encounters. After a task has been assigned for an encounter, for example, a provider preferences engine 250 can retrieve the preferences of the health care provider that submitted the encounter data (e.g., preferences that have previously been submitted through the interface 340, shown in FIG. 3C), for presentation at remote scribe device 106 (e.g., any of remote scribe devices 106*a-n*, shown in FIG. 1), along with the generated transcript and the processed audio file(s). The automatic routing engine 240 and the provider preferences engine 250, for example, can each include software and/or hardware components of the server system 108 (shown in FIG. 1). After the processed encounter data 136 has been provided to a suitable medical scribe, for example, the scribe can generate a clinical note 206 for the encounter, which can be uploaded to the electronic health record (EHR) system 110 (also shown in FIG. 1). Notification of the clinical note 206 having been uploaded to the EHR system 110, for example, can be provided to the practitioner interface device 102, for presentation to the health care provider that submitted the encounter data.

In some implementations, a task type indicated by a health care provider can be used for routing a task (e.g., an operation that is to be performed and completed, based on clinical data for a patient) to a suitable medical scribe or pool of scribes. For example, clinical note generation tasks can be routed to remote scribe devices of medical scribes that are approved to generate clinical notes for the health care provider, and who employ remote scribe interfaces that are configured to facilitate the generation of such notes. As another example, order generation tasks can be routed to remote scribe devices of medical scribes that specialize in processing such orders, and who employ remote scribe interfaces that are configured to process the orders. As another example, referral tasks can be routed to remote scribe devices of medical scribes that specialize in processing referrals, and who employ remote scribe interfaces that are configured to process referrals. In some implementations, a task type indicated by a health care provider can be used as a factor in prioritizing the task. For example, order generation tasks can be assigned a high priority level, as such tasks tend to be more time-sensitive than generating clinical notes. As another example, referral tasks can be assigned a low priority level, as such tasks tend to be less time-sensitive than generating clinical notes.

In some implementations, a medical scribe can be manually assigned to a task for generating a clinical note for an encounter. For example, a manager (e.g., chief scribe who manages a team of scribes) can receive notifications of processed encounter data for various relevant encounters (e.g., encounter data for encounters submitted by health care providers that have been mapped to the chief's team of scribes) being available from the server system 108. The chief scribe can review details of the various encounters and current task queues of the medical scribes on the team, and can manually match tasks for generating encounter notes to suitable scribes.

In some implementations, a medical scribe can self-assign a task for generating a clinical note for an encounter. For example, each medical scribe that has been mapped to the health care provider that submitted the encounter data 132 using the practitioner interface device 102*n* (e.g., medical scribes that have been approved for generating clinical notes for the health care provider) can receive a notification of the processed encounter data 136 being available from the server system 108, through the remote scribe interface 156. A medical scribe can choose to self-assign the task for generating the clinical note for the encounter, for example, and the task can be added to a task queue for the medical scribe. In some examples, a medical scribe can be assigned to multiple ongoing tasks. If the medical scribe were to be unable to complete a current task (e.g., additional information has been requested from the health care provider that submitted encounter data for the task, and the current task has a "Waiting" status), for example, the scribe can self-assign an additional task, and can work on the additional task while waiting for the additional information to arrive for the other task.

In some implementations, a task for generating a clinical note for an encounter can be automatically assigned to a medical scribe. For example, the server system 108 can select, from a group of medical scribes that have been approved to generate clinical notes for the health care provider that submitted the encounter data, a particular scribe to complete the task for generating the clinical note. In general, an automatic assignment of a task can be based on various factors, including a service level of the task (e.g., a due date/time for completing the task), a priority of the task (e.g., whether the a task for completing a clinical note for an encounter has been marked as "STAT" by a health care provider, or whether the task has normal priority), an amount of time remaining in a medical scribe's shift, a current task queue for the medical scribe, an average amount of time the medical scribe takes to complete a task, and/or a task complexity. The various factors can be weighed and balanced for each task and each medical scribe, to identify a preferred scribe for performing the task.

In some implementations, to determine a task complexity, a complexity scoring technique can be used that can include determining complexity scores for various task factors, weighting the complexity scores for the task factors, and determining an overall task complexity score based on the weighted complexity scores for the task factors. Task factors, for example, can include an audio factor, a session flow factor, a specialty factor, an electronic health record (EHR) factor, a care setting factor, a provider preference factor, and other suitable factors. The audio factor, for example, can be based on characteristics of audio files for an encounter (e.g., with tasks for working with relatively long files being given higher complexity scores than for short files, and with tasks for working with files having a relatively large amount of background noise being given higher complexity scores than for files having a small amount of background noise). The session flow factor, for example, can be based on a number of speakers included in the audio for the encounter (e.g., with tasks for working with conversational audio being given higher complexity scores than tasks for working with regular dictation). The specialty factor, for example, can be based on a qualitative assessment of the complexity of each specialty (e.g., orthopedics, internal medicine, etc.), which has been previously determined and stored in a dictionary with key-value pairs. For example, generating clinical notes for encounters for some specialties may be more complex than generating clinical notes for encounters for other specialties. Similarly, the EHR factor can be based on a qualitative assessment of the complexity of working with (e.g., entering notes in) a particular EHR, which has previously been determined and stored in a dictionary with key-value pairs, for example. Similarly, the care setting factor can be based on a qualitative assessment of the complexity of generating clinical notes for a particular care setting (e.g., urgent care, ambulatory, etc.), which has previously been determined and stored in a dictionary with key-value pairs, for example. Similarly, the provider preference factor can be based on a qualitative assessment of the complexity of generating a clinical note according to the preferences that have been specified for a particular health care provider, which has been previously determined (e.g., based on a number of templates referenced in the preferences, a word count of the preferences, and/or other suitable factors) and stored in a dictionary with key-value pairs, for example. After scores for the various task factors have been determined, for example, the scores for the factors can be used to determine an overall complexity score for the task. For example, determining the overall complexity score for the task can include weighting the factors, and performing a computation (e.g., a weighted average, a weighted sum, or another suitable computation) using the weighted factors and associated scores for the factors.

After an overall task complexity score has been determined for a task, the score can be used as a factor in assigning the task to a particular medical scribe, and/or as a factor in determining whether portions of a clinical note for the task may be automatically generated (e.g., with tasks having relatively low complexity scores generally being suitable candidates for automatic note generation). For example, some medical scribes may be specifically trained to work on complex note generation tasks, whereas others may not be trained to work on such tasks. When assigning a complex task (e.g., a task with an overall complexity score that meets or exceeds a threshold value) to a medical scribe, for example, the server system 108 can access the project data source 120, identify a subset of the pool of scribes that have been approved to generate clinical notes for the health care provider and that can be assigned to complex tasks. A suitable medical scribe can be selected from the subset of the pool of scribes and automatically assigned to the task based on one or more other factors, such as a type of task, a due date/time for completing the task, a priority of the task (e.g., whether the a task for completing a clinical note for an encounter has been marked as "STAT" by a health care provider, or whether the task has normal priority), an amount of time remaining in a medical scribe's shift, a current task queue for the medical scribe, and/or a predicted amount of time the medical scribe takes to complete the task (e.g., by multiplying an average amount of time the scribe takes to process a minute of encounter audio data by a total duration of audio files associated with the encounter).

After a task for generating a clinical note has been assigned to a medical scribe (e.g., the task has been manually assigned, self-assigned, or automatically assigned) and the processed encounter data 136 (shown in FIG. 1) has been provided to the medical scribe through the remote scribe interface 156 (also shown in FIG. 1), for example, the scribe can generate a clinical note 206 (shown in FIG. 2) for the encounter. When generating the clinical note 206, for example, the medical scribe can interact with controls of the remote scribe interface 156 to play the one or more processed audio files of the encounter, to reference the transcript of the audio file(s), and to reference the preferences and templates of the health care provider that submitted the encounter data to the server system 108. In general, a clinical note is not a verbatim transcription of what was said during the encounter, but a synthesis of the clinical information conveyed during the encounter (e.g., medical history, observations, diagnosis, treatment plan, etc.), formatted according to preferences and templates of the health care provider. For example, a portion of the remote scribe interface 156 can be used by the medical scribe for working on the clinical note, with easy reference to source information and instructions for generating the note being provided through other portions of the interface.

Referring again to FIG. 1, during stage (E), a completed clinical note 138 can be provided for storage in the health care provider's electronic health record (EHR) system. For example, after the note 138 has been completed by a medical scribe using the remote scribe device 106n, the medical scribe can interact with controls provided by the remote scribe interface 156 to indicate that the note is complete, and the remote scribe device 106n can provide the completed note to the server system 108. In the present example, the server system 108 can then transfer the received completed clinical note 138 to the EHR system 110. As another example, the medical scribe can directly access the EHR system 110, can upload the completed clinical note 138 to the system, and can then use the remote scribe interface 156 to provide a notification to the server system 108 that the upload of the clinical note 138 has been completed. In response to uploading (or receiving a notification that indicates upload of the completed clinical note 138, for example, the server system 108 can update a status of the corresponding encounter (e.g., marking the clinical note for the encounter as being completed and/or uploaded).

During stage (F), a notification 140 that a clinical note for an encounter has been completed and uploaded to the health care provider's electronic health record (EHR) system can be provided to the health care provider. For example, the server system 108 can provide the notification 140 to the practitioner interface device 102n of the health care provider that the completed clinical note 138 has been uploaded to the EHR system 110. After receiving the notification 140, for example, the practitioner interface device 102n can present the notification 140 to the health care provider through the practitioner interface 152.

During stage (G), the health care provider can provide an indication that the completed clinical note for the encounter has been reviewed and approved. If the completed clinical note 138 has been received by the server system 108, for example, the health care provider can use the practitioner interface device 102n to access the note from the server system and review the note. As another example, if the completed clinical note 138 has been uploaded to the electronic health record (EHR) system 110, the health care provider can use the practitioner interface device 102n (or another device) to access the note from the EHR system 100 and review the note. After reviewing the completed clinical note 138 for the encounter, for example, the health care provider can interact with the practitioner interface 152 to indicate that the note has been approved, and a corresponding approval notification 142 can be provided by the practitioner interface device 102n to the server system 108. In response to receiving the approval notification 142, for example, the server system 108 can update a status of the corresponding encounter task (e.g., marking the clinical note for the encounter as being approved).

Referring now to FIGS. 4A-G, example interfaces are shown for facilitating the generation of clinical notes. The example interfaces can be presented by an application (e.g., a web-based application and/or a locally executed application) running on a remote scribe device and in communication with a server system (e.g., server system 108, shown in FIG. 1). Similar to remote scribe interface 156, for example, the example interfaces shown in FIGS. 4A-G can be presented to a medical scribe by any of the remote scribe devices 106a-n (shown in FIG. 1). Example interface 400 (shown in FIG. 4A) can be used in implementations in which tasks for generating clinical notes are manually assigned to the medical scribe and/or self-assigned by the medical scribe. In the present example, interface 400 shows a list of available note generation tasks 402 (e.g., "Available Encounters") that have not yet been assigned to a medical scribe, and a list of note generation tasks 404 that have been assigned to medical scribes and have not yet been completed and approved. The list of available note generation tasks 402 that have not yet been assigned to a medical scribe, for example, can be populated using data provided by the encounter data store 122 and the project data store 120. For example, as new encounter data 132 is received and processed by the server system 108, a task for completing a clinical note can be generated and prioritized, and can be added to the list of available note generation tasks 402, if the task is for an encounter of a health care provider for whom the medical scribe has been authorized to generate notes. In some implementations, a list of available note generation tasks can be sorted in order of when the tasks become available. For example, when a new note generation task becomes available, it can be added to the end of the list 402. In some implementations, a list of available note generation tasks can be sorted according to priority level. For example, when a new note generation tasks becomes available, it can be inserted into a position of the list 402 according to its priority (e.g., with tasks for generating clinical notes for encounters marked by health care providers as being "STAT," tasks for providers having a service agreement that prioritizes such tasks, complex tasks, particular types of tasks, and other prioritized tasks being inserted at or near the top of the list). In the present example, various information can be presented for each task in the list of available note generation tasks 402, such as a health care provider who conducted the encounter, the patient, a number and duration of audio files for the encounter, and a date/time at which the clinical note for the encounter is due. Each task in the list of available note generation tasks 402 can also be associated with a control that initiates the assignment of the task to an operator of the interface 400, or to a different medical scribe.

After a task in the list of available note generation tasks 402 has been assigned to a medical scribe, for example, the task can be removed from the list 402 and can be added to the list of note generation tasks 404 that have been assigned to medical scribes and have not yet been completed and approved. The list of note generation tasks 404 that have been assigned but not yet completed, for example, can be populated using data provided by the encounter data store 122 and the project data store 120. In the present example, various information can be presented for each task in the list of note generation tasks 404, such as a time of last update to the task (e.g., when the task was added to the list, when a status change occurred, and/or when additional data was received for the task), a project for the task, a provider who conducted the encounter, the patient, a number and duration of audio files for the encounter, a date/time at which the health care session was scheduled, a date/time at which the clinical note for the encounter is due, a current status of the task (e.g., assigned, working, waiting, completed and under review, or another suitable status), and a medical scribe to which the task has been assigned. The interface 400 in the present example can also include various controls for searching, filtering, and/or sorting tasks in the list 404, including a control 406 for switching between a view of all tasks in the list, and a view of tasks that have been assigned to a medical scribe who is using the interface 400. In some implementations, a control for switching between views can be provided on an interface operated by a manager or administrator (e.g., a chief medical scribe), and may not be provided on an interface operated by a production worker (e.g., a basic medical scribe). For example, a basic medical scribe can be presented with a view that only lists tasks that have been assigned to the scribe or tasks that can be self-assigned by the scribe. As another example, managers, administrators, and production workers can each be provided with interfaces having controls for switching between views of all assigned tasks or individually assigned tasks.

In some implementations, a task list interface can also present various statistics for tasks and encounters represented by the interface. For example, the interface 400 can be operated by a manager or administrator (e.g., a chief medical scribe), and statistics can be presented for tasks and encounters that pertain to projects being managed. In the present example, multiple projects (e.g., Project A and Project B) are being managed, and for the multiple projects, statistics such as a number of encounters scheduled, a number of encounter tasks received, a number of encounter tasks completed, and a number of online medical scribes that have been approved to work on the tasks can be presented to the manager. In general, the statistics and each of the lists 402, 404 can be dynamically updated as data in the project data store 120 and/or the encounter data store 122 changes over time. For example, as new tasks become available, the tasks can be inserted into the list of available note generation tasks 402 at appropriate locations, and the number of encounter tasks received can be incremented. When a new task is assigned, for example, the task can be removed from the list 402 and added to the list of note generation tasks 404 that have been assigned but not yet completed, with a status of "Assigned." If a task priority changes (e.g., a task with a high complexity score remains in a task queue or a list of available tasks for more than a threshold amount of time), a position in the list 404 can be adjusted toward the top of the list and/or the task can be re-assigned. When a medical scribe begins working on the task, for example, the task's status can be updated to "Working." If additional information has been requested from the health care provider, for example, the task's status can be updated to "Waiting." When the clinical note for the task has been uploaded and is waiting for review, the task's status can again be updated to "Uploaded," for example. When the health care provider has reviewed and approved the clinical note, for example, the task can be removed from the list 404, and the number of completed encounters can be incremented. Real-time interface updating features can be implemented by the server system 108, for example, through a suitable API.

In some implementations, a task list interface can present notifications when new tasks and encounters become available, when additional data for pending tasks and encounters becomes available, and/or when chat messages related to the tasks and encounters are received (e.g., from practitioner interface devices operated by health care providers). For example, an information notification icon 410 and/or a chat notification icon 414 (e.g., one or more visual icons in the upper-right hand corner of interface 400 or another suitable location) can be presented or can visually change (e.g., through an animation, a different appearance, etc.) when new information and/or chat messages are available. In response to a user interaction with (e.g., clicking, hovering over, etc.) the information notification icon 410, for example, an information notification display 412 can be presented (e.g., as a pop-up over the interface 400, adjacent to the interface 400, or another suitable type of presentation). In the present example, the information notification display 412 includes a list of notifications for tasks and encounters that are received during a current shift. The list of notifications, for example, can be ordered by time of receipt (optionally included in the notification), with more recent notifications being presented at the top of the list, and less recent notifications being presented at the bottom of the list. In the present example, the list of notifications includes a notification that new audio is available for an encounter by Provider A1, a notification that the encounter by Provider A1 is overdue, and a notification that a new encounter is available from Provider B2. In response to a user selection of any of the notifications in the list of notifications, for example, the interface 400 can be updated to present additional details for a task or encounter that corresponds to the selected notification (e.g., example interface 430, shown in FIG. 4C). Interactions with the chat notification icon 414 are described in examples below (e.g., example interface 480 shown in FIGS. 4F and 4G).

In some implementations, a task list interface can present a list of clinical note generation tasks that have automatically assigned. For example, interface 420 (shown in FIG. 4B) can include elements similar to that of interface 400 (shown in FIG. 4A), and can be used in implementations in which some or all tasks for generating clinical notes are automatically assigned to medical scribes. In the present example, a list of note generation tasks 424 that have been assigned but not yet completed can be presented for tasks that have been assigned to a medical scribe that is currently using the interface 420 (e.g., Scribe A), per a selection of control 426 (similar to control 406, shown in FIG. 4A) for switching between task list views. As new tasks are automatically assigned to the medical scribe (e.g., by the server system 108), the tasks can be added to an appropriate position in the list 424 (e.g., based on task priority). In some implementations, manual and/or self-assignment of tasks can be disabled when one or more tasks remain in a queue of medical scribe's queue of tasks to be completed, and the medical scribe is not currently waiting for additional encounter information or note approval. In the present example, since "Scribe A" is still working on the task in the list 424, a list of available note generation tasks 422 (e.g., "Available Encounters") can be disabled (or hidden), until such time that the task in the list 242 is completed (or the medical scribe is waiting for additional information/approval). At such time, for example, the list of available note generation tasks 422 can be enabled (or shown), and the medical scribe can be permitted to self-assign one of the tasks.

Figure 4A:
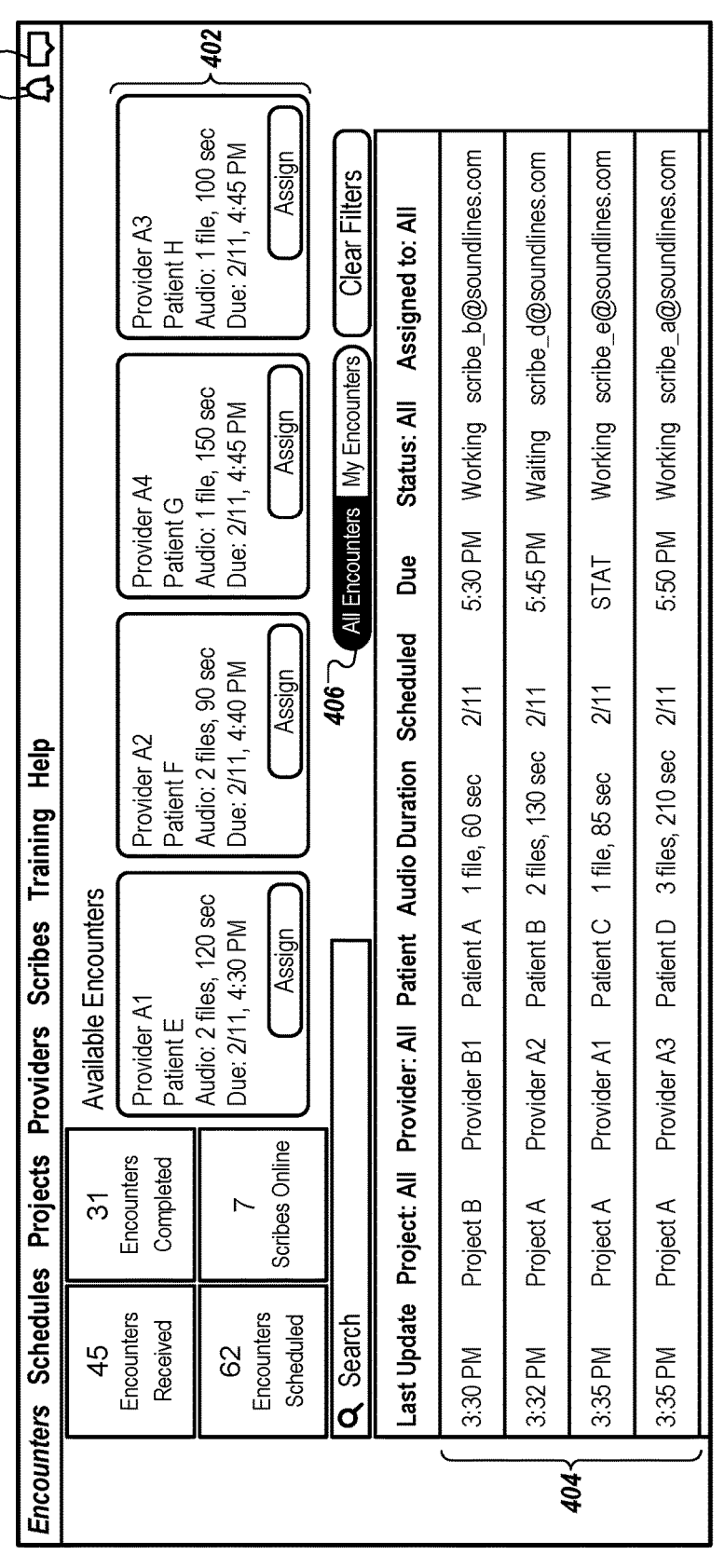
Figure 4B:
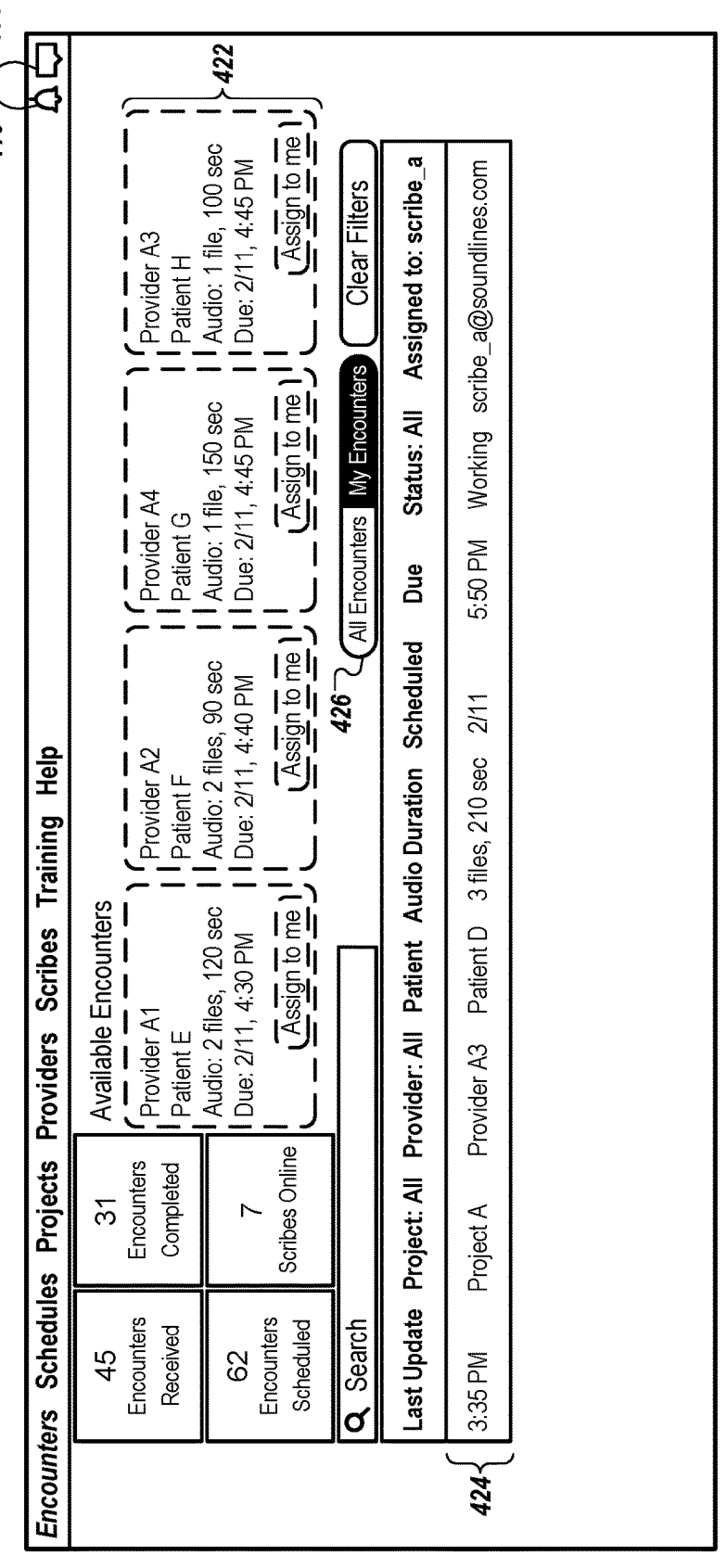
Figure 4C:
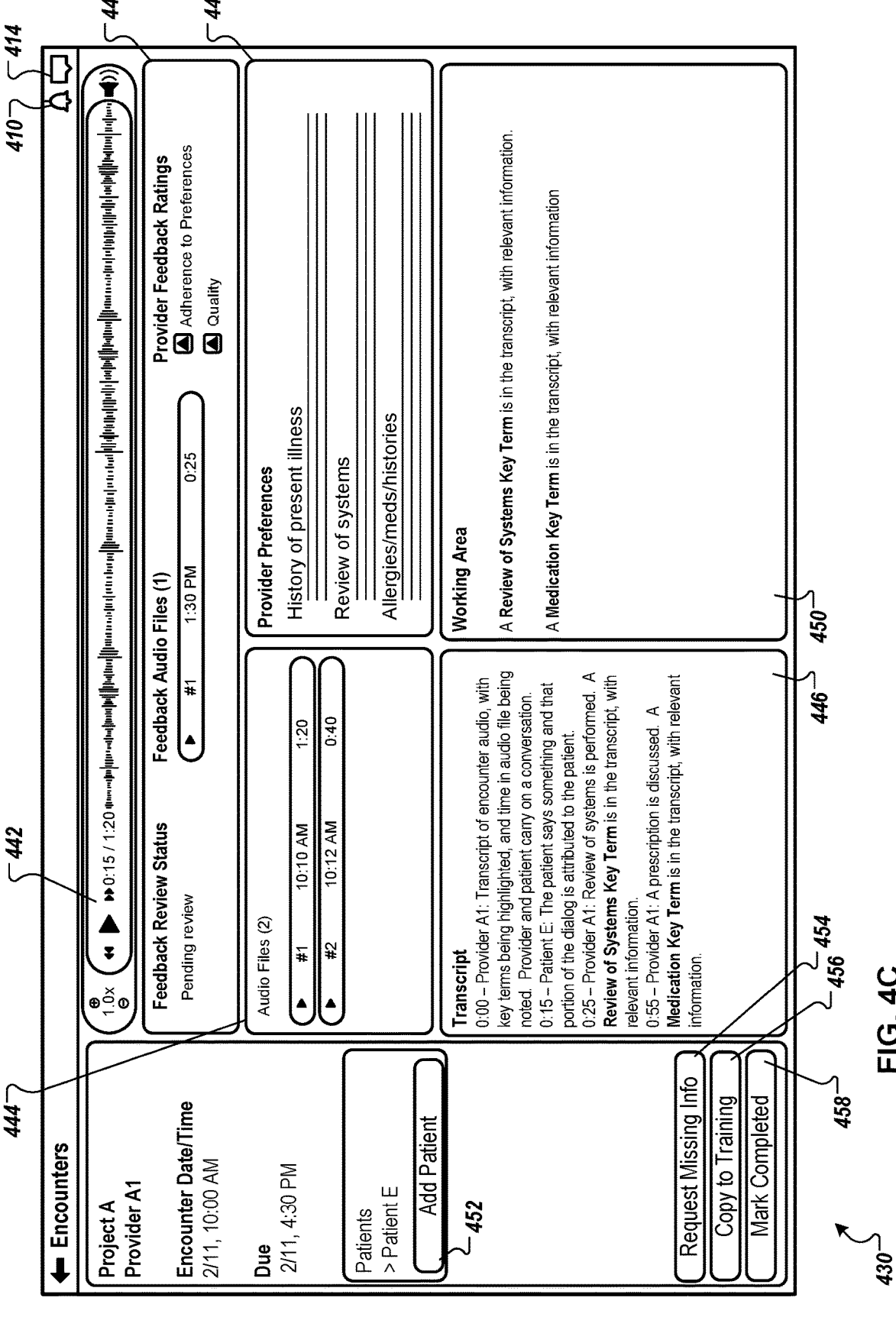
Figure 4E:
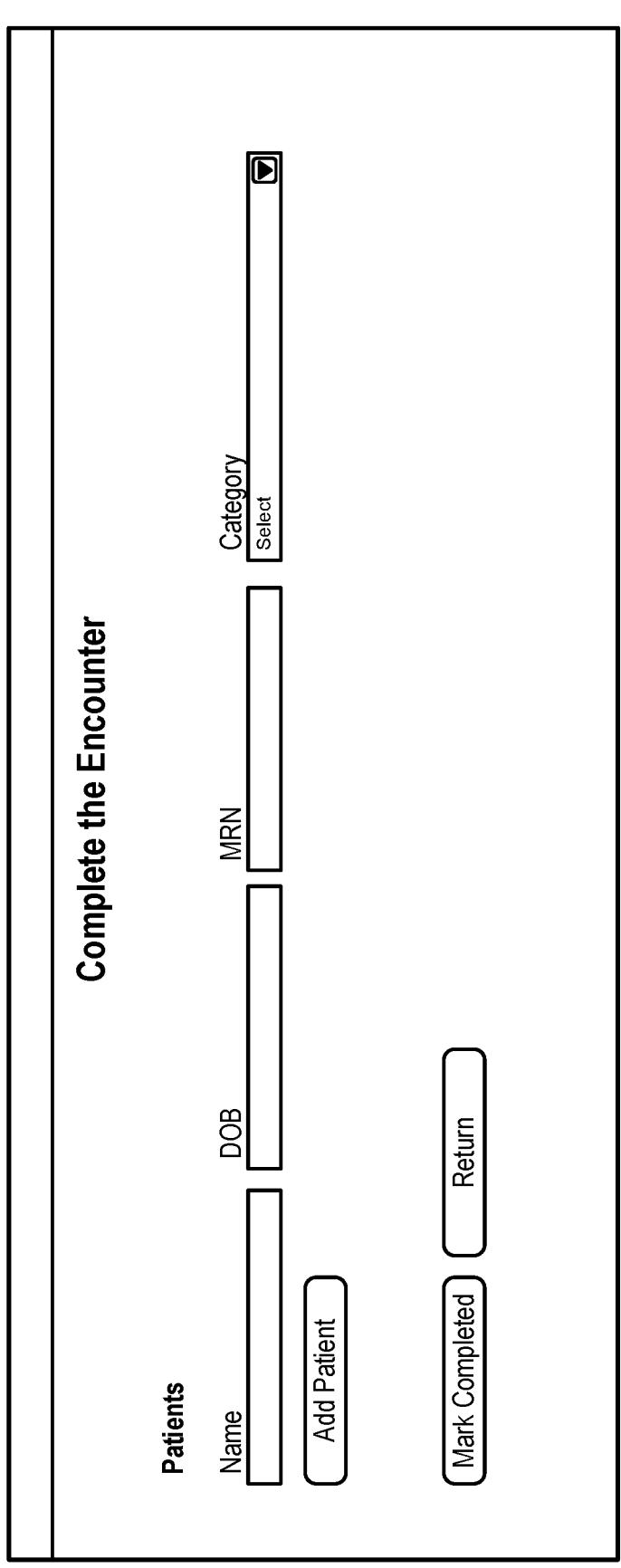
Figure 4E:
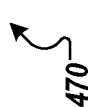

Referring now to FIG. 4C, example interface 430 is shown for working on the generation of a clinical note. In implementations in which tasks can be manually assigned to or self-assigned by medical scribes, for example, selection of a task from a list of clinical note generation tasks can cause the presentation of interface 430. In implementations in which tasks are automatically assigned to medical scribes, for example, a task queue can be maintained for a medical scribe in the background, and interface 430 can serve as a landing page for the scribe (rather than interfaces 400, 420). In the present example, the interface 430 includes one or more notification icons (e.g., information notification icon 410 and/or chat notification icon 414), a media presentation control 442, a media selection control 444, a transcript presentation control 446, a provider preference presentation control 448, a working area 450, a feedback review control 440, an add patient control 452, a request missing information control 454, a copy to training control 456, and a mark completed control 458. The interface 430 in the present example also presents additional information related to the encounter for which a clinical note is to be generated, such as a project for the encounter, a health care provider that conducted the encounter, a date/time of the encounter, and a due date/time for the encounter.

In use, a medical scribe can select a media file (e.g., an audio file, an audiovisual file, etc.) represented in the media selection control 444, and begin playing the media file using the media presentation control 442. The media presentation control 442, for example, can include controls for specifying a playback speed of the file, a control to specify a preferred volume for playback of the file, various file navigation controls (e.g., play, fast forward, fast reverse, etc.), and various file information presentation controls, such as controls that indicate a current time of file playback, a total file duration, and a wave form of the file. To jump to any point in the file playback, for example, the medical scribe can select the point in a seek bar.

The transcript presentation control 446, for example, can present a transcript of the selected file, and can be updated if the medical scribe selects a different file. As another example, the transcript presentation control 446 can present transcripts of all media files represented in the media selection control, in order of the files. In the present example, the transcript presented in the transcript presentation control 446 can be segmented by speaker (e.g., health care provider and patient), with each speaker being labeled in the transcript, and a time within the file at which each speaker speaks also being labeled in the transcript. In some implementations, key terms (e.g., based on a language model) can be automatically highlighted in the transcript. The automatic highlighting of key terms, for example, can be useful to the medical scribe for quickly identifying relevant portions of the transcript and for generating the clinical note. In some implementations, portions of a transcript can be mapped to corresponding portions of a media file. In response to detecting a selection of a portion of the transcript in the transcript presentation control 446, for example, the interface 430 can cause playback of the corresponding portion of the media file through the media presentation control 442. As another example, as the file is being played in the media presentation control 442, a visual indicator (e.g., bold text, highlighted text, automatically scrolled text, or another sort of visual indicator) can indicate a portion of the transcript that corresponds to the portion of media currently being played. The mapping of a transcript to a media file, for example, can be useful to the medical scribe for reviewing important portions of the media file, or verifying portions of a transcript that are potentially incorrect.

In the present example, the provider preference presentation control 448 presents note preferences of the health care provider that conducted the encounter for which a clinical note is to be generated (e.g., preferences that have previously been submitted through the interface 340, shown in FIG. 3C). The medical scribe can review the note preferences (e.g., including templates to be used, formatting instructions, and other sorts of instructions) while generating a draft of the clinical note using the working area 450. In some implementations, portions of a draft clinical note can be pre-generated. For example, one or more templates referenced in the health care provider's preferences can be automatically incorporated into the working area 450, and relevant portions of text from the transcript can be automatically extracted into the template. The medical scribe can review the pre-generated draft clinical note, and edit and add to the note to complete it.

Occasionally, multiple patients may be referenced by a health care provider in a transcript and related media file(s). For example, multiple members of a family may arrive at a health care session conducted by the health care provider. If the health care provider conducted an encounter with multiple patients, for example, the medical scribe can interact with the add patient control 452, which can cause the remote scribe application to present an interface (e.g., interface 470, shown in FIG. 4E) for adding information for each of the additional patients referenced in the transcript/files to the encounter data for the encounter. For example, a patient name, date of birth, medical record number (MRN), and other relevant information can be specified for each patient.

Occasionally, an interference issue with the media file(s) and/or encounter metadata may be present. For example, various elements of the metadata can be missing or incorrect, a quality of the audio in the file can be insufficient, or another interference issue or defect can be present which interferes with the generation of a clinical note. If an interference issue is present, for example, the medical scribe can interact with the request missing information control 454, which can cause the remote scribe application to present an interface (e.g., interface 460, shown in FIG. 4D) for reporting issues with the media file(s) and/or encounter metadata. In the present example, interface 460 includes a set of user input selection controls for indicating interference issues related to patient information (e.g., missing name, incorrect name, missing date of birth, incorrect date of birth, missing medical record number, incorrect medical record number), a set of user input selection controls for indicating interference issues related to specialty statuses (e.g., waiting, missing information), a set of user input selection controls for indicating interference issues related to audio quality (e.g., noisy recording, unclear or inaudible speaking), or other user input selection controls for identifying other defects recognized in the media file(s) and/or encounter metadata. The medical scribe can select corresponding controls for any of the interference issues, and can provide other relevant feedback information.

In response to receiving interference issue reporting data specified by the medical scribe through the interface 460, for example, the server system 108 can change the status of the scribe's task to "Waiting," and can send a corresponding notification to practitioner interface device 102n of the health care provider. The practitioner interface device 102n can present the notification to the health care provider through the practitioner interface application, and the health care provider can address the issues. After the identified interference issue has been addressed, additional encounter data (e.g., including corrected metadata and/or additional media files) can be provided by the practitioner interface device 102n to the server system 108, which can in turn provide a corresponding notification to the remote scribe device 106n of the medical scribe to inform the scribe that additional data for the encounter is available. The notification can include various visual and/or audible elements to alert the medical scribe to new information for currently assigned tasks or newly available tasks for the scribe. In the present example, the information notification icon 410 presented in the upper-right hand corner of interface 430 (or another suitable location) can alert the medical scribe of the new information. The medical scribe can interact with (e.g., click, hover over, etc.) the icon, and a list of recently received notifications (e.g., during the current shift) can be presented to the medical scribe. The scribe can select any of the notifications, for example, and the interface 430 can be updated to present information that pertains to the selected notification (e.g., by navigating to a page for working on a task related to the notification).

Occasionally, an encounter task may be deemed suitable for various training scenarios. For example, a task can be typical (or atypical) of tasks for a particular provider, and a manager (e.g., a chief scribe, an administrator) can decide to maintain information related to the task for training medical scribes. If the manager selects the task for training, for example, the manager can interact with the copy to training control 456, which can cause the remote scribe application to copy the encounter data (e.g., including the metadata, the media files, the transcript, the provider preferences, and contents of the working area) to a training environment (not shown), for use in conducting medical scribe training. As part of a training exercise for a medical scribe, for example, the scribe can access the training environment and generate a clinical note based on the copied training encounter data, and the scribe's note can be compared to a previously generated note which can be considered as a preferred standard. Optionally, portions of the media file and/or the transcript can be annotated to guide trainees in generating a clinical note for the training encounter.

After generating the clinical note, for example, the medical scribe can interact with the mark completed control 458. In response to receiving an indication that the clinical note has been completed, for example, the server system 108 can update a status of the corresponding encounter (e.g., marking the clinical note for the encounter as being completed and/or uploaded). In some implementations, clinical notes can be automatically uploaded to an electronic health record (EHR) system of a health care provider. For example, the server system 108 can transfer a completed clinical note (e.g., from the working area 450) to the EHR system 110 in response to the clinical note being marked as completed through the control 458. In some implementations, clinical notes can be manually uploaded to an EHR system of a health care provider. For example, the medical scribe can manually provide a completed clinical note to the EHR system 110, and afterwards the scribe can mark the clinical note as being completed through the control 458. In some implementations, additional patient information can be collected as part of a process for completing a clinical note. For example, in response to interaction with the mark completed control 458, the medical scribe can be presented with interface 470 (shown in FIG. 4E). In the present example, for each patient that was present at the session, patient information (e.g., name, date of birth, medical record number) can be provided, and a category can be selected. Possible categories, for example, can include a completed chart in an EHR, a provider entering the chart in the EHR, or no EHR note being needed. The categories can be used for billing purposes, for example.

After an encounter task has been marked as completed and the completed clinical note has been reviewed by a health care provider, the health care provider can use the practitioner interface 152 of the practitioner interface device 102 to provide feedback data for the completed clinical note. The feedback data, for example, can be provided by the practitioner interface device 102 to the server system 108, which can then provide some or all of the feedback data to one or more of the remote scribe devices 106a-n. In general, the feedback data can include one or more metric ratings (e.g., including binary ratings, assigned scores, textual ratings, etc.) and/or can include media feedback (e.g., including audio, or both video and audio). The metric ratings and/or media feedback, for example, can pertain to overall note quality (e.g., spelling, grammar, use of correct terminology, etc.), whether the note adheres to preferences specified by the health care provider (e.g., use of specific templates, use of bulleted lists, etc.), and other aspects of the completed note. The feedback data that has been received by the remote scribe device 106 can be presented through the feedback review control 440, for example. In the present example, the health care provider has provided metric ratings that indicate that the completed clinical note is of acceptable quality, and generally adheres to specified preference, and has provided media feedback directed to the clinical note. The feedback review control 440, for example, can be presented when feedback data becomes available, and can be presented by a remote scribe interface operated by a medical scribe that generated the clinical note, a manager of the medical scribe (e.g., a chief scribe), or both. After reviewing the feedback data, for example, an operator of the interface 430 can optionally select the task for training by interacting with the copy to training control 456. As another option, the operator of the interface 430 can update provider preferences (e.g., using interface 340, shown in FIG. 3C), based on the specific content the feedback data. As another option, and as described in examples below, the feedback data can also be used for maintaining quality scores for remote scribes, and for maintaining complexity scores for clinical note generation tasks, to facilitate appropriate future task assignments and scribe training.

In some implementations, received feedback data that pertains to multiple different tasks that have been completed by multiple different medical scribes can be aggregated and presented together in a common interface. For example, a version of the remote scribe interface 156 that is presented to a manager (e.g., a chief scribe who manages a team of scribes) can include a list (not shown) of received feedback data units (e.g., including metric ratings and/or media feedback) for completed tasks. The manager can review and process the feedback data units by selecting items from the list, and/or can flag one or more feedback data units for routing to another manager or administrator.

The medical scribe can be returned to a suitable landing page (e.g., interface 400 or 420 shown in FIGS. 4A-B if tasks are to be at least partially self-assigned, or interface 430 if tasks are to be solely automatically assigned), after the task is complete. The medical scribe can then proceed to work on another task or to end their shift. For example, the remote scribe application can include work schedule features for clocking in and out, and tracking a remaining amount of time in a shift. The encounter data for the completed task can be maintained for a suitable period of time for quality assurance purposes (e.g., three days, a week, a month, or another suitable period of time).

Occasionally, a scenario may arise in which a real-time chat session between a health care provider and a medical scribe (or a group of medical scribes) may be advantageous, to facilitate the completion of a clinical note or another sort of task (e.g., an order of a medication and/or medical service, a referral, etc.). If a health care provider would like to request assistance with generating a new task and/or completing a pending task, for example, the health care provider can use the practitioner interface 152 of the practitioner interface device 102 to initiate a chat session with a particular medical scribe, or with a group of medical scribes that have been assigned to the health care provider (e.g., through the project data store 120). For example, one or more scribes who specialize in facilitating particular types of tasks (e.g., ordering medication, ordering medical services such as imaging, lab tests, etc.) and/or one or more scribes who specialize in responding to chat-based requests can be available for responding to a chat request submitted by the health care provider through the practitioner interface 152. Through the integrated chat features of the remote scribe interface 156, for example, one or more scribes can receive notifications when new messages are added to a chat thread that includes the health care provider and the one or more scribes, and can assist the health care provider with generating and/or completing tasks in real-time by participating in the chat thread.

Figure 4F:
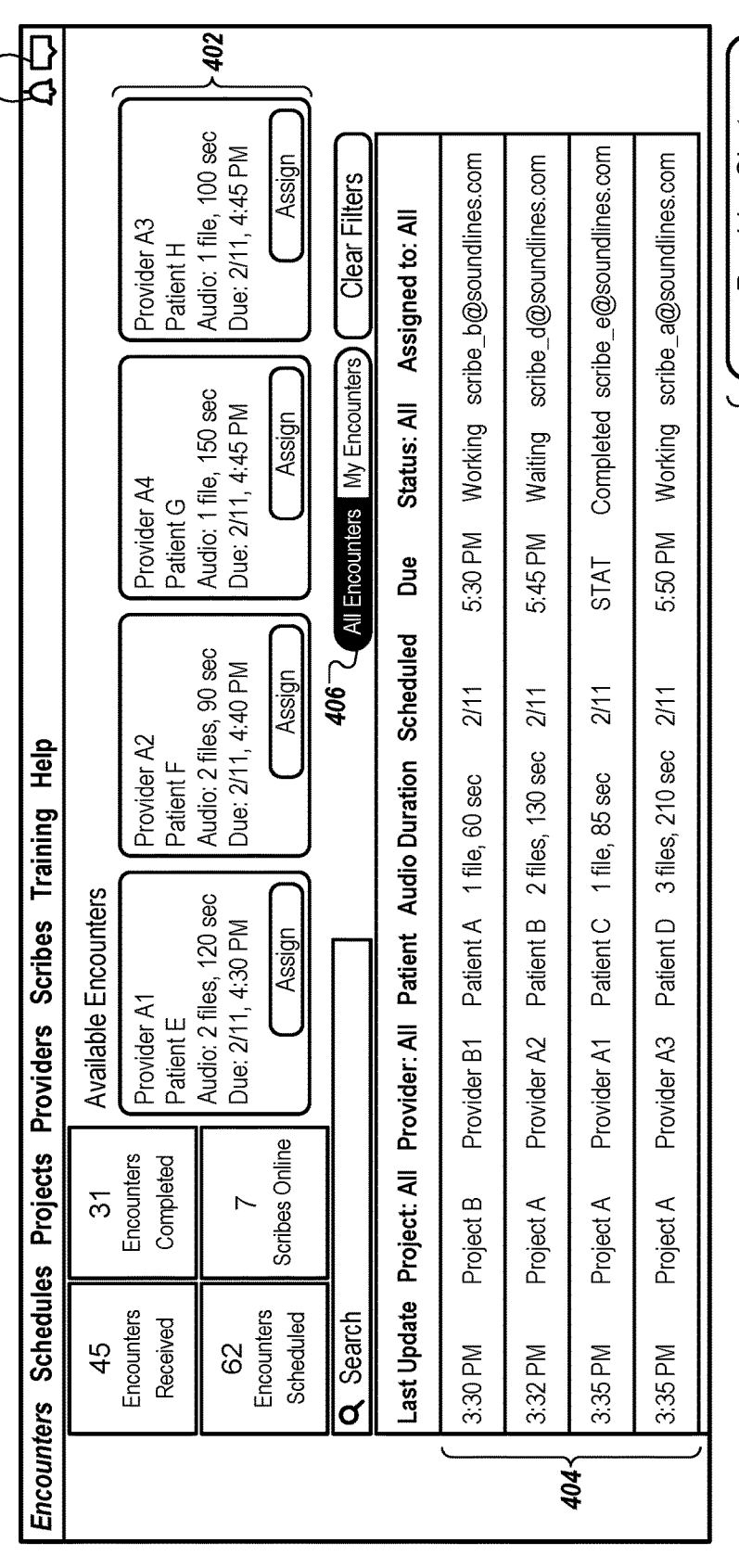

Referring now to FIG. 4F, example interface 480 of the remote scribe interface 156 is shown. Similar to example interface 400 (shown in FIG. 4A), example interface 420 (shown in FIG. 4B), and example interface 430 (shown in FIG. 4C), the example interface 480 includes an information notification icon 410 and a chat notification icon 414. The information notification icon 410 and/or chat notification icon 414 (e.g., one or more visual icons in the upper-right hand corner of interface 480 or another suitable location) can be presented or can visually change (e.g., through an animation, a different appearance, etc.) when new information and/or chat messages are available. In response to a user interaction with (e.g., clicking, hovering over, etc.) the chat notification icon 414, for example, a chat notification display 482 can be presented (e.g., as a pop-up over the interface 480, adjacent to the interface 480, or another suitable type of presentation). In the present example, the chat notification display 482 includes a list of chat thread notifications. Each chat thread notification, for example, can be a selectable list item that represents a corresponding chat thread. Each chat thread, for example, can include chronologically ordered chat messages from different devices, grouped by chat session, health care provider, and/or task. The list of chat thread notifications, for example, can be ordered by time of receipt of the last chat message in the thread (optionally specified in the notification), with notifications representing chat threads with more recent activity being presented at the top of the list, and notifications representing chat threads with less recent activity being presented at the bottom of the list. Additionally, notifications representing chat threads that include one or more unread chat messages can include a visual indication of the chat thread status (e.g., through bolded text, highlighting, animation, etc.). In the present example, the list of notifications includes a notification that a general chat thread for Provider A1 has an unread chat message (e.g., as indicated by bold text and/or a color highlight), along with a portion of the chat message (e.g., "Do I have a scribe working . . . "), and an indication that the last message in the chat thread was received ten seconds ago. The list of notifications in the present example also includes a notification for a general chat thread for Provider A2 (e.g., a chat thread in which all messages have been read, as indicated by normal text), and a notification for a chat thread directed to a particular task (e.g., imaging) for a patient (e.g., Patient F). An operator of the interface 480, for example, can select any of the notifications in the chat notification display 482 to review and participate in a chat thread represented by the selected notification.

Figure 4G:
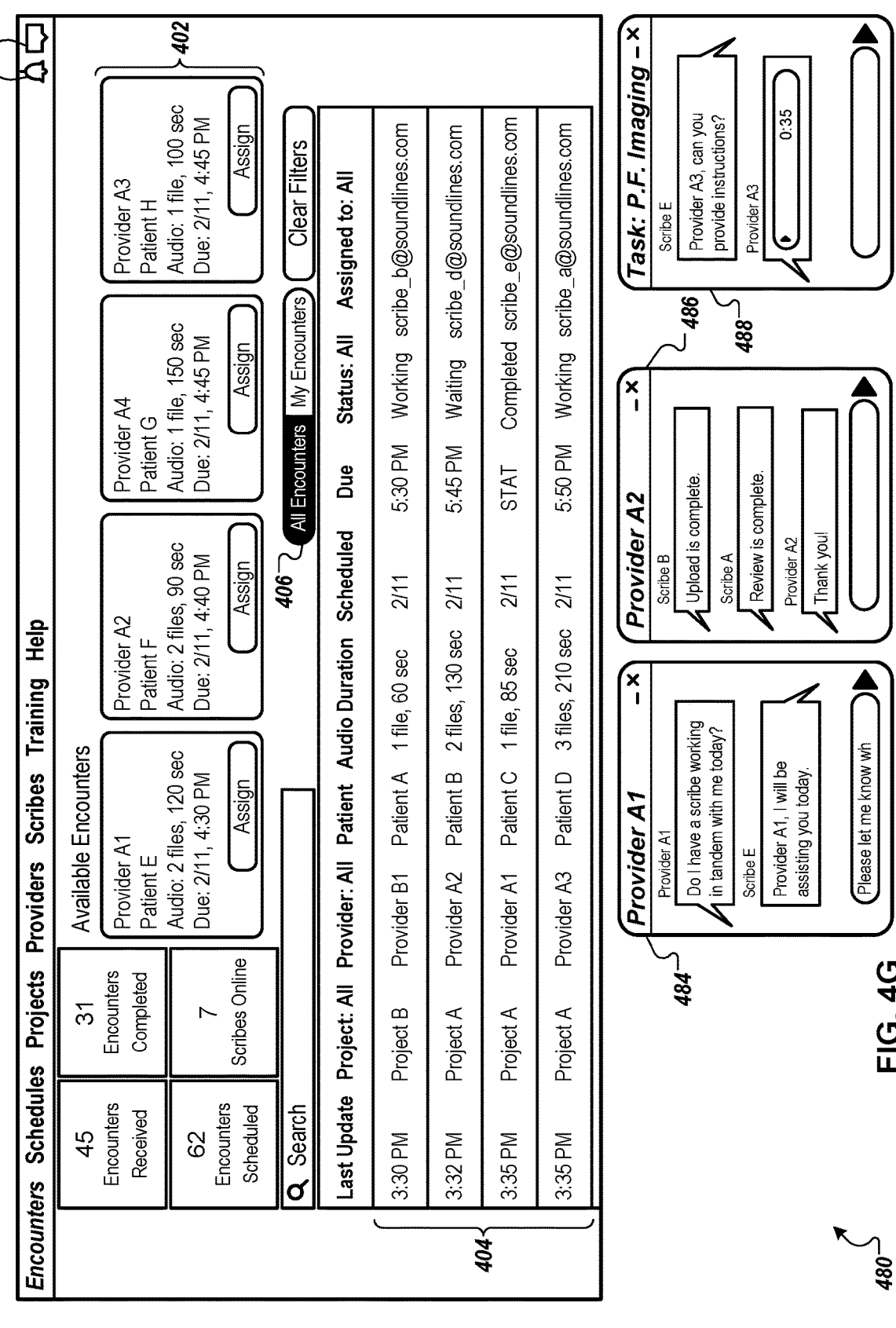

Referring now to FIG. 4G, example interface 480 is shown with multiple chat controls, each chat control being configured to connect to a different ongoing chat session. For example, the operator of the interface 480 can select (e.g., click, hover over, or otherwise interact with) a notification in the list of notification items in the chat notification display 482 (shown in FIG. 4F), and the interface 480 can present a corresponding chat control (e.g., as a pop-up over the interface 480, adjacent to the interface 480, or another suitable type of presentation) for reviewing and participating a chat session represented by the selected notification. In the present example, the operator has selected each of the chat thread notifications in the chat notification display 482. In response to the chat notification selections, for example, the interface 480 can present chat control 484 for a general chat thread for Provider A1, chat control 486 for a general chat thread for Provider A2, and chat control 488 for a task-based chat thread for an imaging task for Patient F.

General chat threads, for example, can be accessed by a health care provider and all medical scribes who have been assigned to assist the provider (e.g., through a project assignment specified in the project data store 120), whereas task-based chat threads can be accessed by a health care provider for whom a task is to be performed and a medical scribe who is assigned to the task (and optionally, one or more managers of the medical scribe). Chat control 484 for the general chat thread for Provider A1, for example, shows an initial chat request (e.g., "Do I have a scribe working in tandem with me today?") that has been broadcast to remote scribe devices 106a-n of multiple different medical scribes who have been assigned to potentially assist Provider A1. In the present example, an operator of the interface 480 (e.g., Scribe E) has responded to chat request (e.g., "Provider A1, I will be assisting you today."), and is currently typing a follow-up message. Chat control 486 for the general chat thread for Provider A2, for example, shows a chat session being conducted by Provider A2 and two medical scribes (e.g., Scribe A and Scribe B) who operate different remote scribe devices than the remote scribe device currently presenting interface 480. Chat control 488 for the task-based chat thread for the imaging task for Patient F, for example, shows a chat session being conducted by Provider A3 and Scribe E (e.g., the operator of the interface 480). In the present example, Scribe E has requested instructions, and Provider A3 has provided the instructions as media data (e.g., including audio data, or both audio and video data) rather than typed instructions. By providing multiple discrete chat threads, for example, and by organizing the chat threads by provider and by task, multiple ongoing communications can be effectively managed through an integrated remote scribe interface. Additional examples of providing communications from the perspective of the remote scribe device and a practitioner interface device are described below.

Figure 5A:
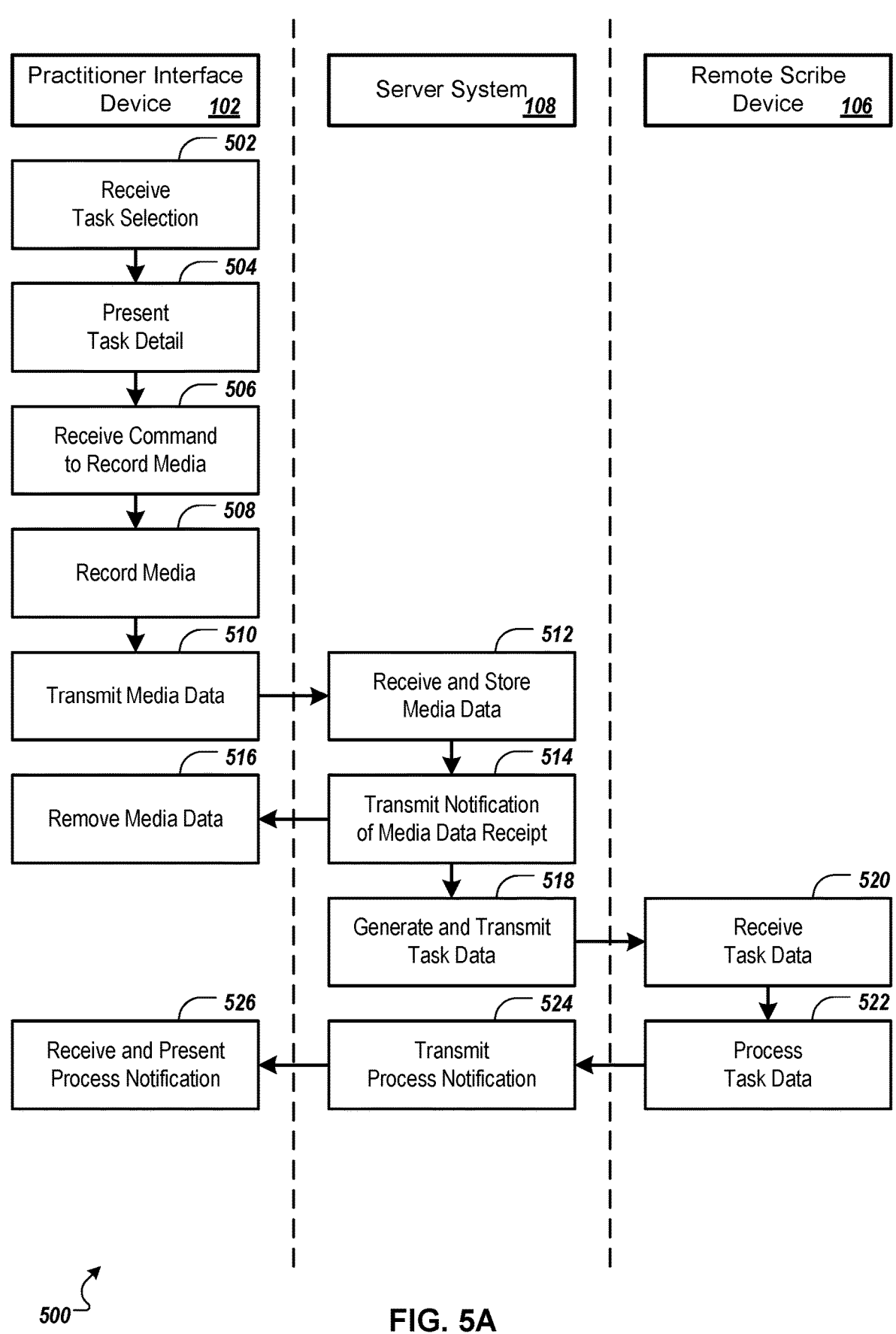
FIGS. 5A-C is a lane diagram of an example technique for facilitating communication in a clinical service environment.
Figure 5B:
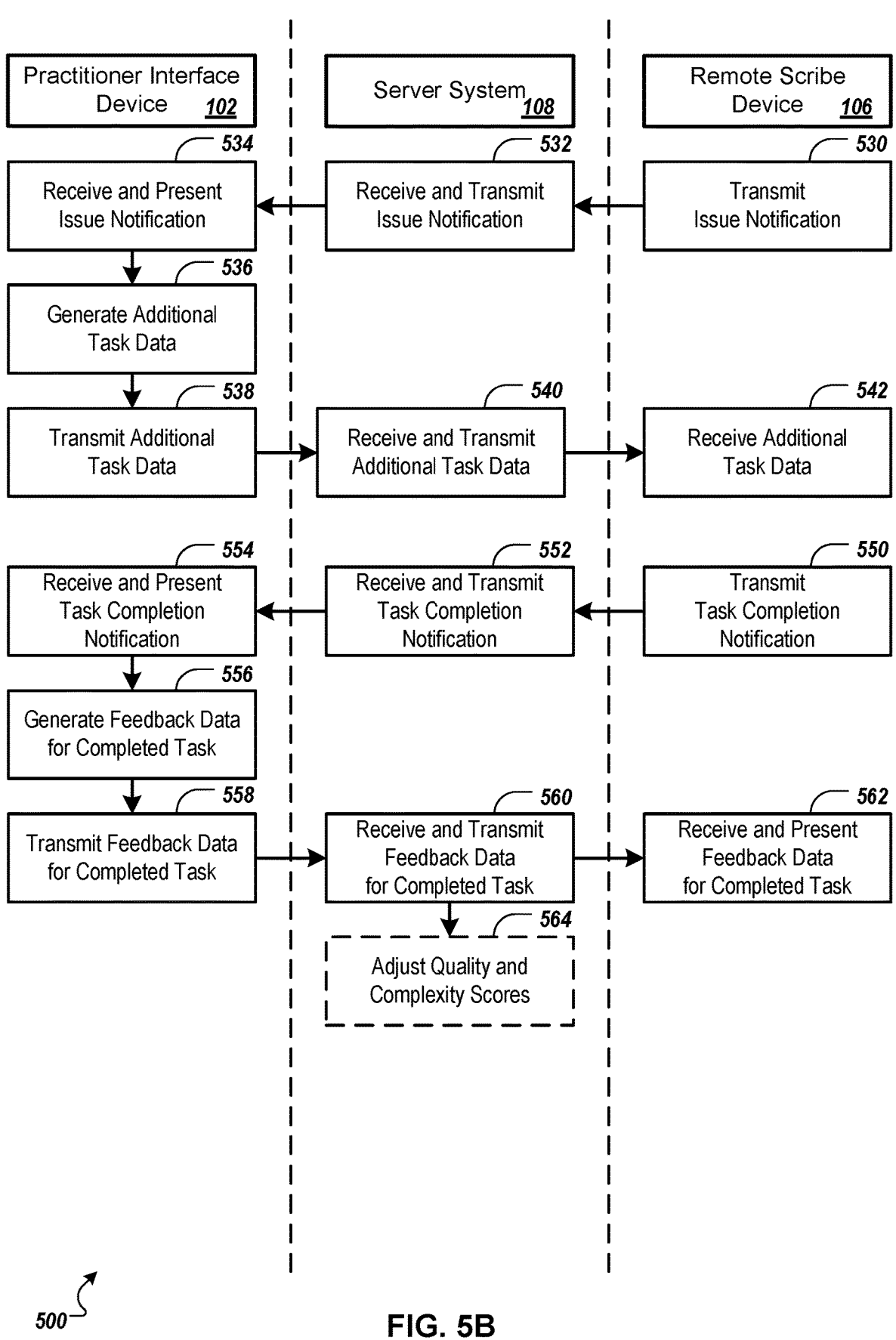
Figure 5C:
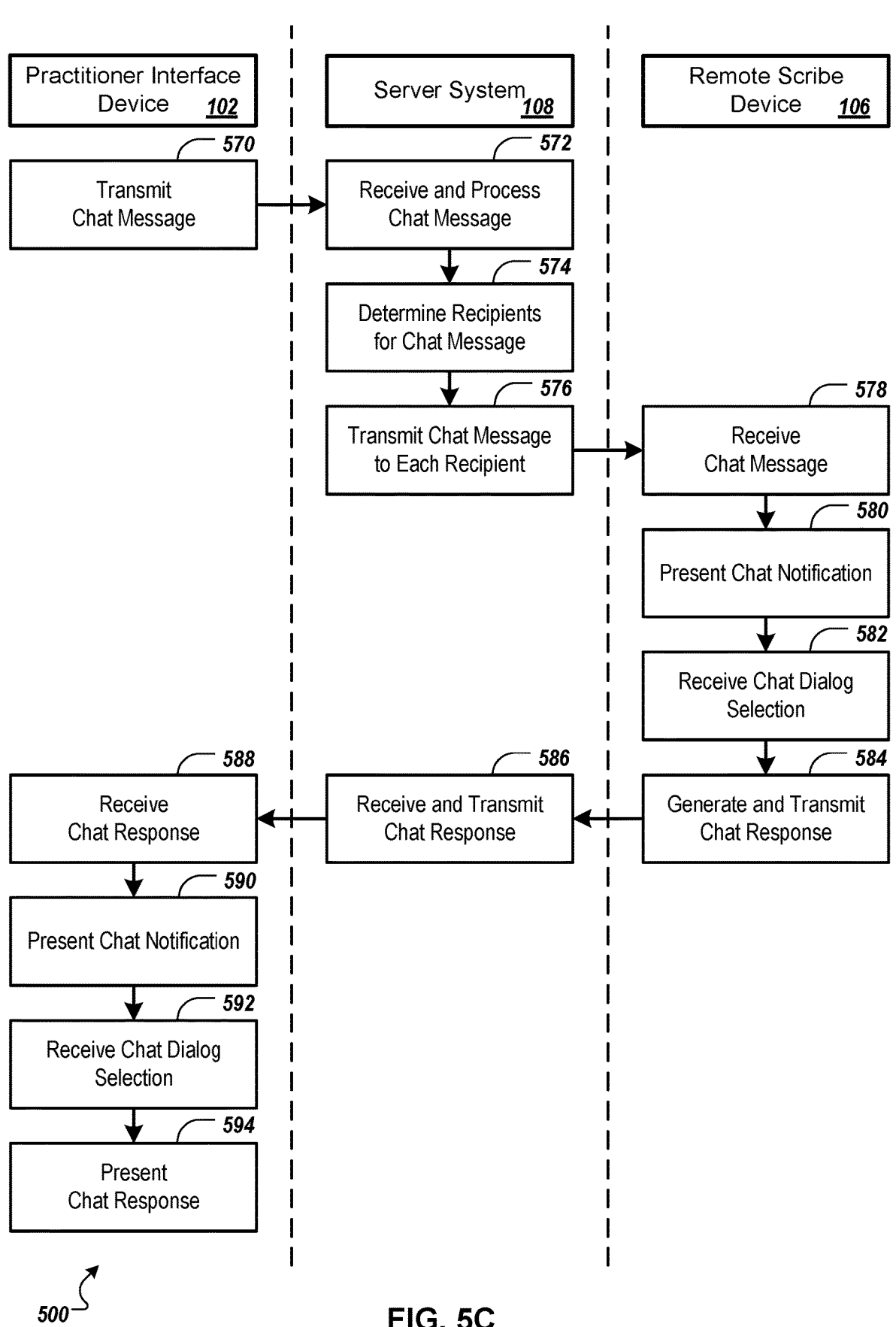

FIGS. 5A-C is a lane diagram of an example technique 500 for facilitating communication in a clinical service environment. In general, the example technique 500 can optionally include operations for transmitting media data (e.g., including audio data, or audio and video data, or media data in combination with other recorded information) by a practitioner interface device, transforming the media data into encounter data that can facilitate the completion of a task (e.g., the generation of a clinical note, or another sort of task) by a remote scribe device, and transmitting various notifications to the practitioner interface device that indicate the status of the task as it is being processed. Further, the example technique 500 can optionally include operations for transmitting interference issue notifications (e.g., notifications that indicate a data defect that interferes with completion of the task) to the practitioner interface device, and for transmitting additional/updated encounter data to the remote scribe device. Further, the example technique 500 can optionally include operations for transmitting task completion notifications (e.g., notifications that indicate that a task has been completed and that a generated work product for the task is ready for review) to the practitioner interface device, and for transmitting feedback data to the remote scribe device. Further, the example technique 500 can optionally include operations for initiating and conducting a chat session between a practitioner interface and one or more remote scribe interfaces. Since the generation of clinical notes and the performance of other tasks in a clinical environment generally involves private patient data, an integrated system in which inter-application communication is handled as part of a workflow can maintain data security while maintaining high standards for the generated work product. In the present example, the technique 500 can be performed by the server system 108 (shown in FIG. 1), remote scribe device 106 (e.g., any of remote scribe devices 106a-n, also shown in FIG. 1), and practitioner interface device 102 (e.g., any of practitioner interface devices 102a-n, also shown in FIG. 1).

Figure 6A:
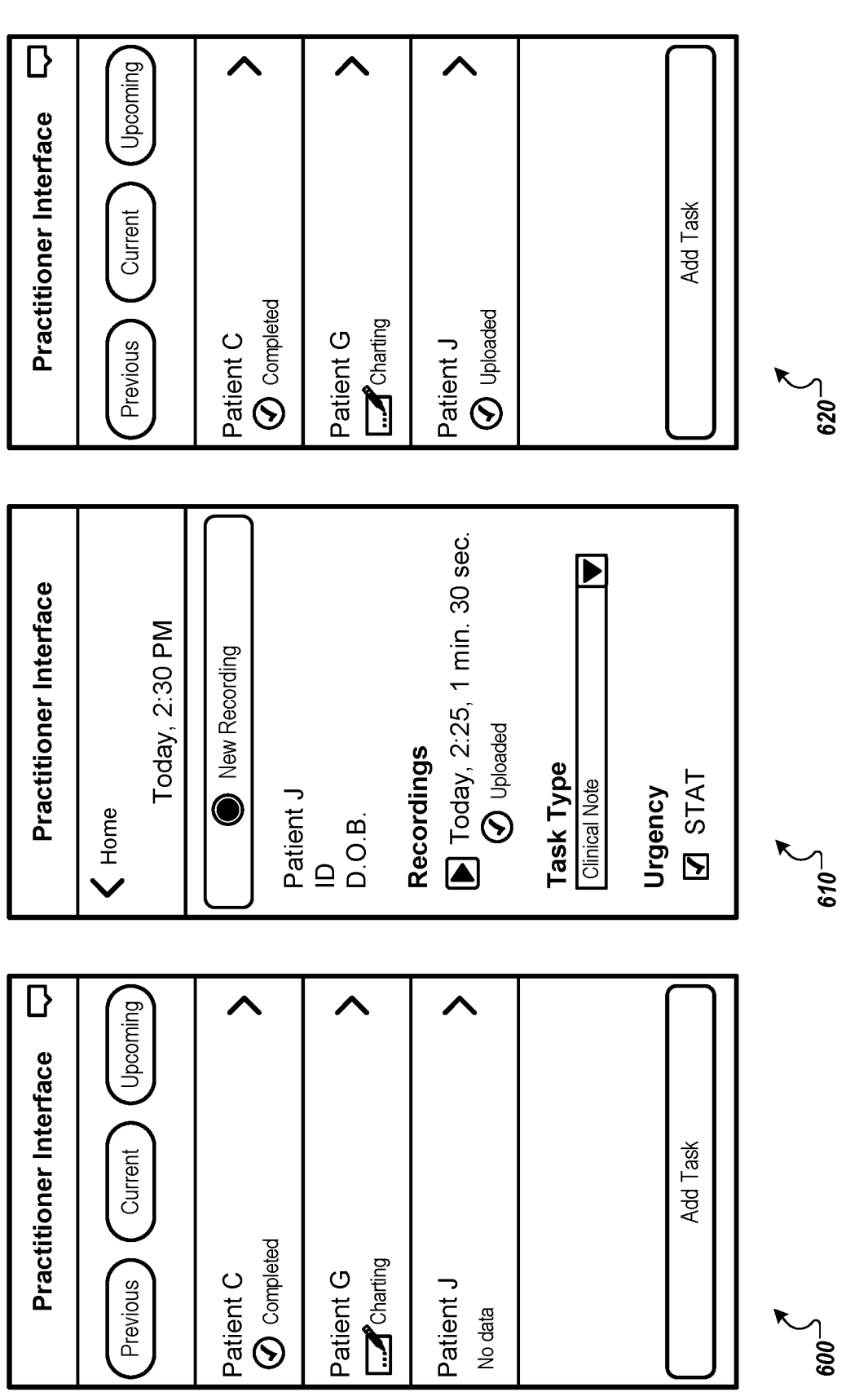
FIGS. 6A-C depict example interfaces for providing clinical note data and managing communications with remote scribes.

A practitioner interface device can receive a task selection (502). Using the practitioner interface device 102, for example, a health care provider can select a task (e.g., a note generation task for a health care session with a patient, an order task for placing a medical service for the patient, a referral task for referring the patient to another health care provider, etc.). In general, data representing tasks can be generated by the practitioner interface device 102 (e.g., under the operation of a health care provider), and/or can be generated by another device that is in communication with the server system 108 (e.g., one of the remote scribe devices 106a-n or a different device under the operation of a medical scribe, an administrative assistant, etc.). Referring now to FIG. 6A, for example, screen 600 of a practitioner interface (e.g., practitioner interface 152, shown in FIG. 1) includes a list of tasks, a series of controls for navigating to tasks for previous, current, and upcoming time periods, and a control for adding a new task to the list (e.g., an "Add Tasks" control). In the present example, the screen 600 shows list items for three different tasks-a note generation task for Patient C, a note generation task for Patient G, and a note generation task for Patient J. In some implementations, an indication of current task status can be included with a list item. For example, the note generation task for Patient C has been completed and is ready for review (e.g., "Completed"), whereas the note generation task for Patient G is currently being worked on by a medical scribe (e.g., "Charting"), and the note generation task for Patient J presently has no data. As task data is processed by devices in the system 100, for example, notifications can be provided to the practitioner interface device 102, and task statuses can be updated in the practitioner interface 152, thereby giving the health care provider a real-time view of pending and completed tasks.

The practitioner interface device can present task detail (504). For example, the health care provider can select the note generation task for Patient J from the screen 600, and the practitioner interface device 102 can update the practitioner interface 152 to present screen 610. In the present example, screen 610 of the practitioner interface 152 includes patient information (e.g., patient name, patient identifier, patient date of birth, etc.), an indication and/or selection control for a task type (e.g., the clinical note generation task), a control for indicating tasks urgency (e.g., "STAT," or normal urgency), and a control for recording media data to document the health care session (e.g., "New Recording").

The practitioner interface device can receive a command to record media data (506), and in response, the practitioner interface device can record media data (508). For example, the health care provider can use the practitioner interface device 102 to dictate information to be included in a clinical note for a patient (e.g., Patient J). In the present example, the health care provider can select the control for recording media data on the screen 610, and practitioner interface device 102 can begin recording media data (and optionally, visual data) in response to the selection. In some implementations, a practitioner interface can present a graphical indicator that displays recording feedback (e.g., audio levels, recording time, etc.) while recording the media data (not shown). The health care provider can select a control on the screen 610 (e.g., a recording control which toggles from "New Recording" to "End Recording") to end the recording, and in response, the practitioner interface device 102 can stop recording media data and can generate a file that includes the media data.

The practitioner interface device can transmit the media data to a server system (510). For example, after generating the file that includes the media data, the practitioner interface device 102 can present information related to the generated media file on the screen 610 (e.g., a date/time stamp of when the file was generated, a length of the file, and other relevant file information), and can automatically begin transmitting the media file to the server system 108. In some implementations, resumable upload techniques can be used to transmit the media file, for example, such that a file upload to the server system 108 can resume from a last point of upload (rather that from the beginning), if the file upload is interrupted at any point (e.g., due to a faulty network connection). As the file is being transmitted, an upload status indicator can be updated to inform a user of the practitioner interface device 102 of the current status as the status changes (e.g., "Generating File," "Uploading," etc.). In some implementations, the media data can be transmitted along with metadata associated with a session, provider, and/or patient. For example, the practitioner interface device 102 can provide to the server system 108 encounter data 132 (shown in FIG. 1) that pertains to the health care provider (e.g., an operator of the practitioner interface device 102) and a patient. The encounter data 132, for example, can include media data (e.g., one or more session recordings recording during and/or after the session), and can include various metadata for the encounter/task.

The server system can receive and store the transmitted media data (512), and in response, the server system can transmit a notification of receipt of the media data, to the practitioner interface device (514). For example, the server system 108 can receive the transmitted media file(s) and the optional metadata from the practitioner interface device 102 and can store the file(s) and the metadata. After the media file(s) (and optional metadata) have been received and stored, for example, the server system 108 can transmit a media data receipt notification to the practitioner interface device 102 that indicates that the data has been received and stored.

The practitioner interface device can remove the media data from local storage (516). For example, in response to receiving the notification from the server system 108 that media data has been successfully received and stored, the practitioner interface device 102 can automatically delete the transmitted media file from local storage of the practitioner interface device 102, thus freeing up storage resources. Further, in the present example, the practitioner interface device 102 can update the file upload status indicator on the screen 610 (e.g., to "Uploaded") for the uploaded media file for the task for Patient J. If a healthcare provider later requests to review the media file through the practitioner interface 152, for example, the media can be streamed by the server system 108 to the practitioner interface device 102, rather than the device 102 playing a locally stored media file. By storing and playing media data through the server system 108, for example, sensitive patient data can be secured at a central server location.

The server system can generate and transmit task data (518). After receiving and storing the encounter data 132 (including the media data and optional metadata) from the practitioner interface device 102, for example, the server system 108 can perform various audio processing, speaker segmentation, and speech-to-text operations on the audio portion of the media data to generate a transcript, as described in further detail above with respect to stage (C) (shown in FIG. 1) and the components of FIG. 2. Optionally, the server system 108 can retrieve and/or generate additional task metadata related to the session, provider, and/or patient. In the present example, the task metadata (e.g., metadata specified through the practitioner interface device 102 and/or retrieved by the server system 108 from the projects data store 120) can include a provider project identifier (e.g., an identifier for a group of health care providers and associated medical scribes), a provider specialty (e.g., orthopedics, internal medicine, or another sort of specialty), a provider electronic health record (EHR) system, a provider care setting (e.g., urgent care, ambulatory, etc.), a provider location, a provider service level (e.g., a turnaround time for task completion), a session priority (e.g., "STAT" tasks vs. normal priority tasks), a session media duration (e.g., a total duration of all media for a session), and a session flow (e.g., an indication of a conversation between a provider and a patient, an indication of dictation performed by the provider, etc.). Other examples may include more metadata, less metadata, or different types of metadata. The processed media data (and optionally, the original media data), the generated transcript, and the optional task metadata can be stored by the server system 108 using the encounter data store 122. The server system 108 can transmit the task data (e.g., including associated metadata, one or more processed media files, and a transcript based on the media files) to a suitable remote scribe device 106, for example, using various automated assignment and routing techniques, as described in further detail above with respect to stage (D) (shown in FIG. 1) and the components of FIG. 2.

A remote scribe device can receive the task data (520). For example, the remote scribe device 106 can receive the task data from the server system 108 after the assignment and routing techniques have been performed. After receiving the task data, for example, the remote scribe device 108 can present at least a portion of the data at the remote scribe interface 156 (shown in further detail in FIG. 4C), to facilitate performance of the task (e.g., the generation of a clinical note or another sort of task).

The remote scribe device can process the task data (522), and the server system can transmit a process notification to the practitioner interface device (524). For example, an operator can begin working on the task (e.g., using the remote scribe interface 156 to generate a clinical note or perform another sort of task), and in response, the remote scribe device 106 can transmit a notification to the server system 108 that work on the task is in progress. As another example, use of the remote scribe interface 156 can be detected by the server system 108 through a direct data connection between the server system 108 and the remote scribe device 106. When work on the task is in progress, for example, the server system 108 can transmit the process notification to the practitioner interface device 102 that provided the task data.

The practitioner interface device can receive and present the process notification (526). For example, the practitioner interface device 102 can receive the process notification from the server system 108, and in response, can present an indication of the process notification to an operator of the practitioner interface device 102. Referring again to FIG. 6A, for example, screen 620 shows that the media file (and optional metadata) for a task associated with patient J has been uploaded, and that a task associated with Patent G is currently being processed (e.g., "Charting"), which provides an operator of the practitioner interface device 102 real-time information about specific operations being performed on various different remote scribe devices (e.g., remote scribe devices 106a-n) and the statuses of each task.

The remote scribe device can transmit an interference issue notification to the server system (530). For example, when a task (e.g., the generation of a clinical note or the performance of another sort of task) is being processed, an interference issue with media data (e.g., media file(s)) and/or metadata may be present, such as missing and/or incorrect metadata, insufficient audio quality, or another sort of interference issue or defect that interferes with performance of the task. Referring again to FIG. 4D, interface 460 (e.g., a screen of the remote scribe interface 156) can be presented by the remote scribe device 106 for collecting data that indicates issues with the media files(s) and/or metadata for a task. Interface 460, for example, includes user input selection controls for indicating interference issues related to patient information, specialty statuses, audio quality, or other defects in the media files and/or metadata. In the present example, a medical scribe who is working on the task can indicate a specific interference issue (e.g., a missing MRN for Patient G), and can flag the issue using interface 460. In response to an operator using the interface 460 to flag one or more interference issues, for example, the remote scribe device 106 can transmit the interference issue notification (e.g., including data that indicates the specific issues and/or defects) to the server system 108.

Figure 6B:
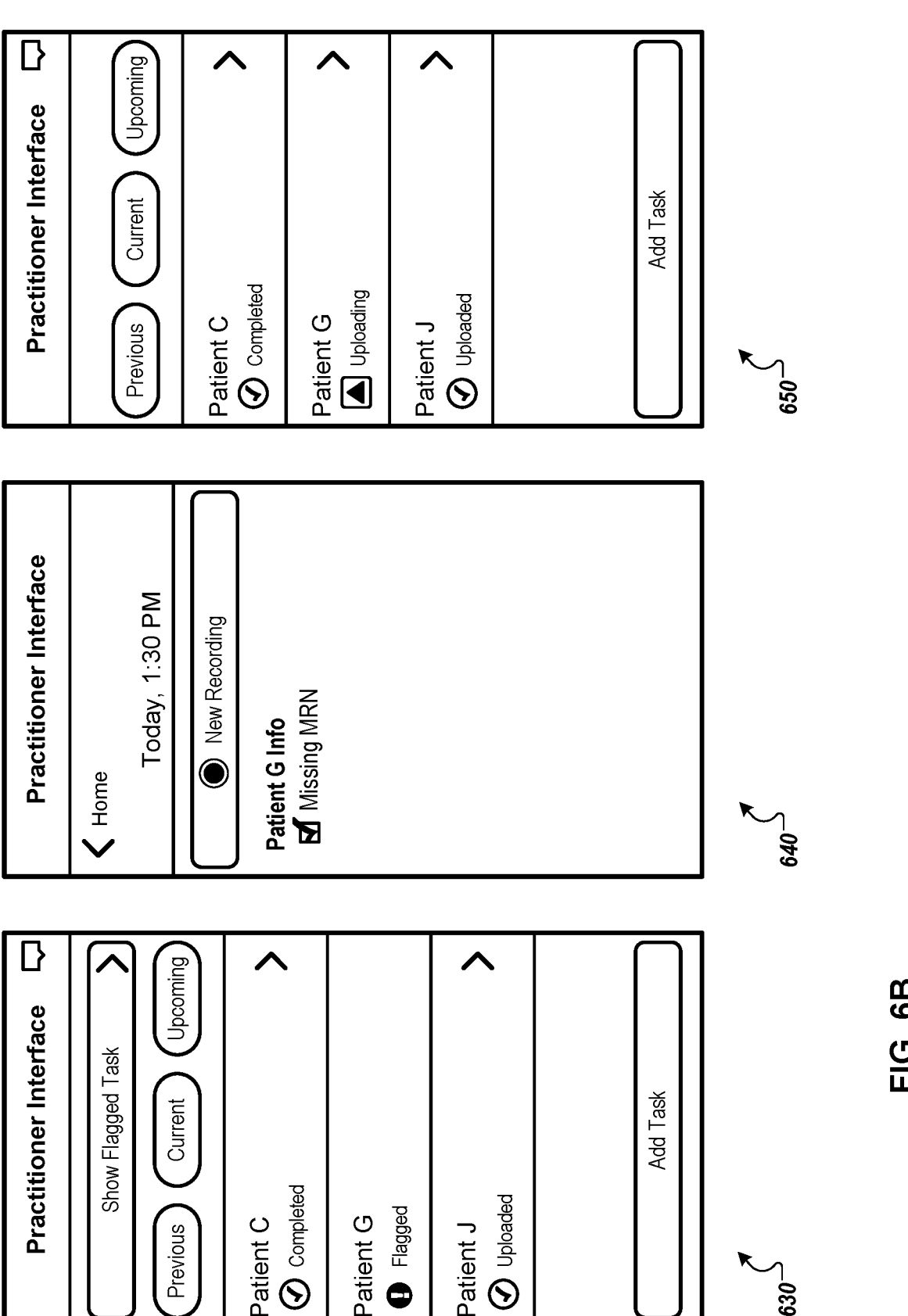

The server system can receive the interference issue notification and can transmit the notification to the practitioner interface device (532), which can in turn receive the interference issue notification from the server system, and can present the notification (534). For example, the server system 108 can receive the interference issue notification (e.g., including the data that indicates the specific issues and/or defects) from the remote scribe device 106, and can then transmit the interference notification to the practitioner interface device 102 which had provided the task data for the remote scribe device 106. In response to receiving the notification, for example, the practitioner interface device 102 can present an indication (e.g., visual, audio, and/or tactile) that the notification was received. Referring to FIG. 6B, for example, screen 630 of the practitioner interface 152 can present one or more visual indications of the interference issue notification received from the server system 108. In the present example, the patient/task list of screen 620 (shown in FIG. 6A) has been modified as screen 630 (shown in FIG. 6B) to include a control labeled "Show Flagged Tasks," and to include an updated task status indicator for the note generation task for Patient G (e.g., "Flagged"), to notify an operator of the practitioner interface 152 that an interference issue exists. The operator of the practitioner interface 152 in the present example can select the control to "Show Flagged Tasks" and/or can select the note generation task for Patient G, and in response, the practitioner interface 152 can be updated to present screen 640 (shown in FIG. 6B).

The practitioner interface device can generate additional task data (536). For example, an operator of the practitioner interface 152 can review information that has been sent with the interference notification that indicates the specific issues and/or defects with the task data, and can use the interface 152 to specify one or more corrections to the task data (e.g., additional media file(s), updated metadata, etc.). The operator of the practitioner interface device 102, for example, can refer to screen 640 to receive information about the specific problem which caused the interference issue (e.g., a missing MRN for Patient G). The screen 640, for example, can include controls for updating the task metadata, such as text entry/correction controls, media recording controls, etc. In the present example, the health care provider can provide input (e.g., corrected text input and/or recorded media input) that corrects the interference issue, and can re-submit the task data using the practitioner interface 152.

The practitioner interface device can transmit the additional task data to the server system (538). Transmission of the additional task data by the practitioner interface device 102 to the server system 108, for example, can involve similar techniques as described above at (510)-(518). In the present example, the practitioner interface 152 can be updated to present screen 650 (shown in FIG. 6B), which shows that task data for the task for Patient G is now "Uploading."

The server system can receive the additional task data from the practitioner interface device, and can transmit the additional task data to the remote scribe device (540), and the remote scribe device can receive the additional task data from the server system (542). For example, the server system 108 can receive the additional task data from the practitioner interface device 106, and can in turn transmit the additional task data to the remote scribe device 106 (after optionally processing and/or enhancing the additional task data as described above at (510)-(518)). After receiving the additional task data, for example, the remote scribe device 106 can present a notification to an operator of the device 106 that the interference issue has been corrected, and the operator (e.g., a medical scribe) can again work on completing the task. In response to continued work on the task (e.g., a selection or auto-assignment of the task and/or use of the interface 430, shown in FIG. 4C), for example, the remote scribe device 106 can transmit a notification to the server system 108 that the task is again in progress. The server system 108, for example, can transmit the process notification to the practitioner interface device 102 that provided the task data, and the practitioner interface device 102 can receive the process notification and can present an indication of the process notification to the device operator (e.g., by updating the list item representing the task for Patient G at screen 650 to "Charting").

The remote scribe device can transmit a task completion notification to the server system (550). For example, after completing a task, the operator of the remote scribe device 106 can use the remote scribe interface 156 to indicate that the task has been completed, and in response, the remote scribe device 106 can transmit the task completion notification to the server system 108. In the present example, the operator of the remote scribe device 106 can interact with the mark completed control 458 of the interface 430 (shown in FIG. 4C) to indicate that the task has been completed.

Figure 6C:
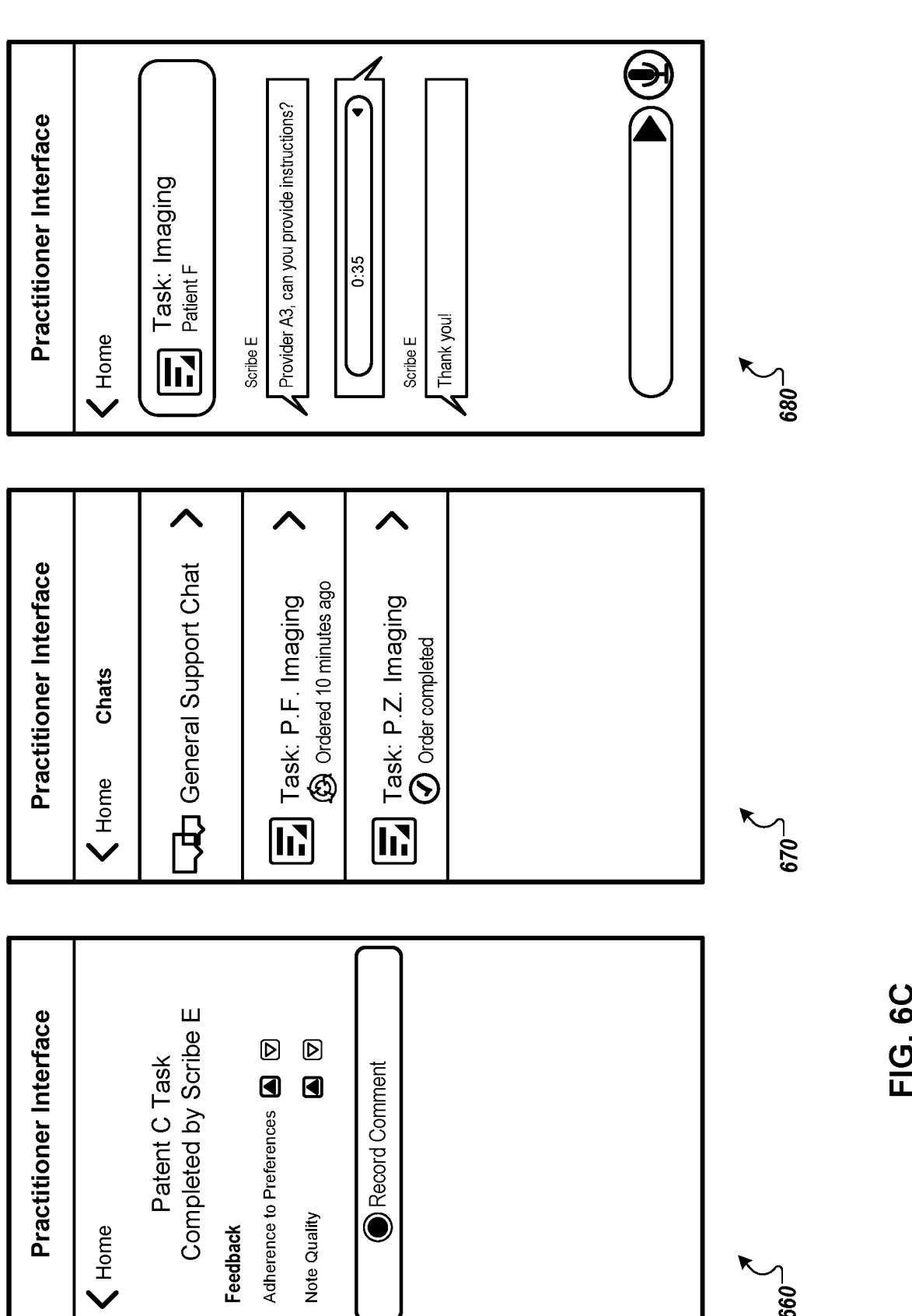

The server system can receive the task completion notification and can transmit the notification to the practitioner interface device (552), which can in turn receive the task completion notification from the server system, and can present the notification (554). For example, the server system 108 can receive the task completion notification from the remote scribe device 106, and can then transmit the task completion notification to the practitioner interface device 102 which had provided the task data for the remote scribe device 106. In response to receiving the notification, for example, the practitioner interface device 102 can present an indication (e.g., visual, audio, and/or tactile) that the notification was received. Referring again to FIG. 6A, for example, screen 600 of the practitioner interface 152 can present a visual indication of the task completion notification received from the server system 108 at a selectable control that represents the task. For example, the screen 600 can include a control (e.g., a list item) that represents the note generation task for Patient C, which includes a task status indication that has been updated based on the received task completion notification (e.g., "Completed"), to notify an operator of the practitioner interface 152 that the task has been completed. The operator of the practitioner interface 152 in the present example can select the note generation task for Patient C from the task list, and in response, the practitioner interface 152 can be updated to present screen 660 (shown in FIG. 6C).

The practitioner interface device can generate feedback data for the completed task (556). For example, an operator of the practitioner interface 152 can review information associated with the completed task (e.g., a completed clinical note, or a completed work product for another sort of task), using the practitioner interface 152 or another interface. Review of the work product for the completed task is described in further detail above with respect to stage (G) (shown in FIG. 1). After reviewing the work product, for example, the device operator (e.g., the health care practitioner) can use integrated feedback controls for easily providing feedback data for a task to which the feedback data pertains. In general, the feedback data can include one or more metric ratings and/or can include media feedback for the work product for the completed task. The metric ratings and/or media feedback, for example, can pertain to an assessment of overall note quality, whether the note adheres to preferences specified by the health care provider, and other aspects of the completed note. In some implementations, generating feedback data for a completed task can include collecting one or more metric ratings (e.g., including binary ratings, an assigned score, textual ratings, etc.) for the work product for the completed task. For example, the operator of the practitioner interface 152 can interact with one or more ratings specification controls to provide the metric ratings. In the present example, the operator can provide input (e.g., by interacting with ratings specification controls on the screen 660) to specify that the generated clinical note adheres to the health care provider's preferences, and that note quality is acceptable. In some implementations, generating feedback data for a completed task can include collecting recorded media feedback that pertains to a review of the work product for the completed task. For example, the operator of the practitioner interface 152 can interact with a recording control (e.g., the "Record Comment" control on the screen 660) to provide a review of the work product which clarifies the metric ratings.

The practitioner interface device can transmit the feedback data for the completed task to the server system (558). Transmission of the feedback data by the practitioner interface device 102 to the server system 108, for example, can involve similar techniques as described above at (510)-(518). The server system can receive the feedback data for the completed task from the practitioner interface device, and can transmit the feedback data to a remote scribe device (560), and the remote scribe device can receive the feedback data for the completed task from the server system, and can present the feedback data to a device operator (562). For example, the server system 108 can receive the feedback data from the practitioner interface device 102, and can in turn store the feedback data in association with the completed task (e.g., for future quality and complexity scoring), and transmit the feedback data to one or more of the remote scribe devices 106*a-n* (e.g., a remote scribe device a manager of the worker who performed the task, the remote scribe device of a worker who performed the task, or respective remote scribe devices of both the worker and the manager). Referring again to FIG. 4C, for example, the interface 430 can present the feedback data specified by the health care provider for the completed task, at the feedback review control 440. In the present example, the metric ratings specified by the health care provider using the screen 660 (shown in FIG. C) can be presented through the feedback review control 440 (e.g., that the generated clinical note is of acceptable quality and adheres to specified preferences), and the recorded media that pertains to the review of the work product for the completed task can be made available through a playback control.

Optionally, the server system can adjust quality and complexity scores, based at least in part on the feedback data (564). In general, feedback data can be used to maintain quality scores for remote scribes, and to maintain complexity scores for clinical note generation tasks, to facilitate task assignments and training. For example, when positive feedback data is received for a work product for a task performed for a health care provider, a quality score for the worker who performed the task can be increased and/or a complexity score for future tasks for the health care provider can be decreased (e.g., if the provider's ratings are more positive than an average provider). As another example, when negative feedback data is received for a work product for a task performed for a health care provider, a quality score for the worker who performed the task can be decreased and/or a complexity score for future tasks for the health care provider can be increased (e.g., if the provider's ratings are more negative than an average provider).

When routing task data to one or more of the remotes scribe devices 106*a-n* (and/or when automatically assigning a task), for example, the server system 108 can retrieve and/or generate the quality score of the remote scribe and the complexity score of the task, along with authorization information of the remote scribe (e.g., identifiers for types of encounters for which the scribe is authorized to perform tasks), and can use the scribe quality score, the task complexity score, and the authorization information when performing the routing operations (e.g., during stage (D), above). In general, the authorization information for a scribe can be updated as the scribe receives additional credentials and/or training. For example, a scribe can be authorized to work on tasks for one or more particular provider projects, provider specialties, and/or tasks that involve working with particular electronic health record (EHR) systems.

A scribe's quality score can generally be based on various scribe metrics that are collected over time, as the scribe completes tasks in the clinical data platform. The scribe metrics, for example, can include an average or median amount of time for the scribe to complete a task, an average or median time spent reviewing media for a task, training completed by the scribe for various provider specialties (e.g., orthopedics, internal medicine, or other sorts of specialties), training completed by the scribe for various sorts of electronic health record (EHR) systems, scribe access to EHR systems, scribe availability (e.g., hours/day, hours/week, etc.), and/or quality ratings of tasks completed by the scribe (e.g., based on provider feedback and/or manager ratings). Other examples may include additional scribe metrics, fewer scribe metrics, or different scribe metrics.

In some implementations, a quality score for a scribe can be determined by performing a computation (e.g., a weighted average, a weighted sum, or another statistical computation) based on the various scribe metrics. For example, each scribe metric can be assigned a corresponding qualitative or quantitative value. Suitable weighting factors (e.g., values from zero to one) can be qualitatively determined for each scribe metric, the weighting factors can be applied to the scribe metric values, and the weighted values can be aggregated. Aggregated scribe quality scores can include numeric values (e.g., values from zero to one, or another suitable range of values), assigned label values (e.g., high, medium, low, etc.), binary values, or other suitable values. Quality scores can be maintained for each scribe (e.g., in memory, data storage, etc.), and optionally, at least a portion of a scribe's quality score can be determined at a time that it is to be used by the server system. For example, scribe metrics can change over time, as a scribe works on and is evaluated for completing tasks. By retrieving up-to-date scribe metrics and computing a current quality score for a scribe, for example, the server system can dynamically adjust to changing conditions in a work environment.

In some implementations, multiple different quality scores can be maintained for a remote scribe, and each quality score can pertain to a different encounter factor (or combination of encounter factors). For example, a scribe can have a first quality score for tasks involving a first specialty (e.g., orthopedics), a second quality score for tasks involving a second specialty (e.g., internal medicine), and so forth. The specialties and the associated quality scores for tasks involving the specialties, for example, can be non-specific to particular providers. As another example, a scribe can have a first quality score for tasks that involve working with a first EHR system, a second quality score for tasks that involve working with a second EHR system, and so forth. Retrieving a quality score of the remote scribe can include retrieving/computing the quality score (from the multiple different quality scores) that pertains to the encounter factor of the health care session for which the scribe may be assigned a task. Thus, a customized and prioritized set of tasks can be determined for each scribe in a pool of scribes, based on factors related to the tasks and based on particular skills of the scribes.

Occasionally, a health care provider may want to request assistance with generating a new task and/or may want to communicate with an assistant to facilitate completion of a pending task. To provide communication between the health care provider and various different remote assistants, for example, the practitioner interface 152 can integrate chat functionality with the task workflow. For example, the health care provider can use the practitioner interface 152 of the practitioner interface device 102 to participate in a chat session with a particular assistant (e.g., a medical scribe), or a group of assigned assistants (e.g., assistants who are associated with the health care provider through the project data store 120). One or more assistants who specialize in performing certain tasks (e.g., ordering medication, ordering medical services such as imaging, lab tests, etc.) can be available for handling chat-based requests and communications submitted by the health care provider through the practitioner interface 152.

The practitioner device can transmit a chat message to the server system (570), and the server system can receive and process the chat message (572). In the present example, the health care provider can access screen 670 (shown in FIG. 6C), and can select a control that represents a chat thread (e.g., a general chat thread, a task-based chat thread, or another sort of chat thread) from a list of multiple ongoing chat threads. General chat threats, for example can be accessed by a health care provider and all assistants who have been associated with the provider (e.g., through a project assignment specified in the project data store 120), whereas task-based chat threads can be accessed by the health care provider for whom the task is to be performed and an assistant for the task (and optionally, one or more managers). In response to selection of the control that represents the task-based chat thread for performing an imaging task for Patient F, for example, the practitioner interface 152 can present screen 680. As shown in screen 680, for example, an assistant (e.g., Scribe E) who is currently working on the imaging task has requested instructions for performing the task (e.g., "Provider A3, can you provide instructions?"). In response to the request, for example, the health care provider can interact with one or more communication controls (e.g., text input controls, media recording controls, data selection controls, etc.) and can provide data for communicating in the selected chat thread. In the present example, the health care provider selects a media recording control and records spoken instructions for Scribe E to facilitate performance of the imaging task for Patient F. As another example, the health care provider can use the screen 680 of the practitioner interface 152 to provide text instructions. After the communication data has been received through practitioner interface 152, for example, the practitioner interface device 102 can transmit the chat message that includes the communication data, to the server system 108.

Figure 5D:
FIG. 5D is a flow diagram of an example technique for receiving and processing chat messages.

Referring now to FIG. 5D, a flow diagram of an example technique for receiving and processing the chat message (572) is shown. In general, some requests that are submitted through a chat message can be automatically handled by the server system 108, whereas other requests are routed to one or more remote scribe devices 106. By intercepting chat messages, determining which chat messages include requests that can be automatically handled, and selectively routing the chat messages based on the determination, communications between practitioner interface devices 102 and remote scribe devices 106 can be streamlined and simplified, while securing sensitive patient data.

Each chat message that is received (572a) by the server system 108, for example, can be analyzed by a text recognition component (e.g., a natural language processing (NLP) component that performs text recognition based on human language modeling, including statistical, machine learning, and/or deep learning models) and a semantic meaning of the chat message can be determined (572b). For example, a chat message submitted by a health care provider can include a request for a particular sort of task to be performed (e.g., "Please order a blood panel for this patient," or "I would like a blood panel," etc.). In the present example, the text recognition component can determine that the semantic meaning of the request is that the health care provider is requesting that the particular task (e.g., a blood panel) be performed for their current patient. In some implementations, a confidence score can be generated for a determined semantic meaning. For example, if a chat message includes the request "Please order a blood panel for this patient," the text recognition component can generate a high confidence value that the semantic meaning of the request is that a blood panel is to be performed for the health care provider's current patient, whereas if the chat message includes the request "I would like a blood panel," the text recognition component can generate a moderate confidence value that the semantic meaning of the request is that the blood panel is to be performed for the patient.

A determination can be performed of whether the semantic meaning of the chat message is mapped to a task for which one or more automated actions can be performed (572c). For example, the server system 108 can access an automated task data store (not shown) that maps possible semantic meanings of chat-based requests to tasks that have been automated. Some tasks (e.g., general requests for assistance, requests for complex tasks to be performed, infrequent requests, etc.) may not be represented in the automated task data store, whereas other tasks (e.g., commonly requested tasks, requests for simple tasks and/or information, etc.) may be represented in the automated task data store and associated with computer instructions for automatically performing the task. In some implementations, a determination of whether a semantic meaning of the chat message is mapped to an automated task is performed when the confidence score for the semantic meaning meets a threshold value. For example, if the confidence score for the semantic meaning of the chat-based request meets the threshold value (e.g., 90%, 95%, 99%, or another high value), the determination can be performed, whereas if the confidence score does not meet the threshold value, the determination is not performed.

If the semantic meaning of the chat message is mapped to one or more automated tasks, for example, an automated response can be transmitted to a sender of the chat message (272d), and the automated task(s) can be performed (272e). For example, if the server system 108 determines that the semantic meaning of the chat-based request "Please order a blood panel for this patient" is mapped to one or more automated tasks, the server system 108 can send an acknowledgement message (e.g., "Order for blood panel received for Patient A—in processing") to the sender of the chat message (e.g., the practitioner interface device 102) for presentation by the practitioner interface 152. In the present example, the server system 108 can execute the computer instructions for automatically performing actions that are associated with the task (e.g., ordering a blood panel for a patient), including accessing metadata (e.g., one or more identifiers, etc.) of a patient encounter being accessed through the practitioner interface 152, submitting one or more requests through an application programming interface (API) of the electronic health record (EHR) system 110, and optionally sending one or more automated status messages (e.g., "Order for blood panel for Patent A has been placed") to the practitioner interface device 102 that report status updates as the task actions are being performed and completed.

In some implementations, when a chat-based request is automatically processed and handled, a chat message that triggered the automatic processing and handling can be intercepted and not forwarded to the originally intended recipients. For example, if the server system 108 determines that the chat-based request "Please order a blood panel for this patient" is to be automatically handled, it can perform the actions of the automated task without transmitting any messages to the remote scribe device 106. In some implementations, when a chat-based request is automatically processed and handled, the chat message that included the chat-based request can be forwarded to one or more remote scribe devices 106 that were originally intended to receive the chat message, along with a notification that the request is being automatically processed. When status updates for task actions being performed and completed are generated, for example, automated status messages can be transmitted to the practitioner interface device 102 and to the remote scribe device(s) 106.

If the semantic meaning of the chat message is not mapped to one or more automated tasks, for example, recipients for the chat message can be determined and the chat message can be transmitted to the determined recipients (272f). For example, if the server system 108 is unable to determine the semantic meaning of the chat message, or if the semantic meaning is determined but is not mapped to an entry in the automated task data store, or if the semantic meaning is determined and is mapped to an entry, but a confidence value of the semantic meaning does not meet a threshold value, the server system 108 can forward the chat message to remote scribe devices 106a-n of assistants who can handle a chat-based request included in the chat message. Example techniques for facilitating chat communications between the practitioner interface device 102 and the remote scribe device(s) 106 are described in further detail below.

Referring again to FIG. 5C, the server system can determine one or more recipients for the chat message (574). For a general chat thread, for example, the server system 108 can access the project data store 120, and can identify the remote scribe devices 106a-n of assistants who have been assigned to participate in chat sessions with the health care provider who used the practitioner device 102 to transmit the chat message. For a task-based chat thread, for example, the server system 108 can access metadata associated with the selected task-based chat thread (e.g., a health-care provider identifier, an assistant identifier, a task identifier, etc.), can access the project data store 120 and/or the encounter data store 122, and can identify one or more remote scribe devices 106a-n of assistants who have been assigned to the task (e.g., the assistant who is working on the task, and optionally, the assistant's manager). In the present example, the server system 108 can determine that the recipient for the chat message transmitted by the practitioner interface device 102 (e.g., operated by Provider A3) is the remote scribe device 106 (e.g., operated by Scribe E).

The server system can transmit the chat message to each recipient (576). For example, the server system 108 can transmit the chat message that includes the communication data specified through the practitioner interface 152 of the practitioner interface device 102, to each remote scribe device 106 that is associated with an assistant who has been determined as a recipient of the chat message. In the present example, the remote scribe device 106 of Scribe E (e.g., the assistant who has been assigned to work on the imaging task for Patient F) can be a recipient of the transmitted chat message (and optionally, a remote scribe device of the assistant's supervisor). If the chat message were to be designated for a general chat thread, for example, the server system 108 can transmit the chat message for receipt by each of the remote scribe devices that are associated with assistants who have been assigned to the health care provider (e.g., through a project assignment specified in the project data store 120).

In some implementations, a chat message can be initially transmitted to a single recipient or (a limited group of recipients), and can later be transmitted to another recipient (or an expanded group of recipients). For example, the server system 108 can initially transmit the chat message to an assigned assistant (e.g., Scribe E), and can start a response timer in the background (e.g., for five minutes, fifteen minutes, or another length of time). If a response to the chat message has not been received within an amount of time corresponding to the response timer, for example, the server system 108 can then transmit the message to another recipient (e.g., Scribe E's manager) or the expanded group of recipients (e.g., other assistants who are associated with the health care provider according to data maintained in the project data store 120).

The remote scribe device can receive the chat message (578), and in response, can present a chat notification (580). For example, the remote scribe device 106 can receive the chat message, and can present a notification that that the chat message has been received, through the remote scribe interface 156. Referring again to FIG. 4F, for example, the interface 480 can present (or modify) the chat notification icon 410 in response to receipt of the chat notification of receipt of the chat message. In the present example, an operator of the interface 480 (e.g., Scribe E) can interact with the chat notification icon 410, and in response the interface 480 can present the chat notification display 482.

The remote scribe device can receive a chat dialog selection (582). For example, the chat notification display 482 can include a list of chat thread notifications, each chat thread notification being a list item that represents a corresponding ongoing chat thread in which an operator of the remote scribe device 106 can participate. In the present example, the chat thread notification for the chat thread for the imaging task for Patient F can include an indication of a recently received unread chat message (e.g., through bolded text, highlighting, animation, etc.), an amount of time that has elapsed since the last chat message in the thread (e.g., one minute), and at least a portion of the last chat message (e.g., "Here are your instructions."). The portion of the last chat message, for example, can be a portion of text, and can include a text transcription of a recorded media file. In the present example, the operator of the interface 480 (e.g., Scribe E) can select a notification item in the chat notification display 482 (e.g., the list item that is associated with the task-based chat thread for the imaging task for Patient F), and in response, the interface 480 can present a corresponding chat control (e.g., as a pop-up, an adjacent display, or another type of presentation) for reviewing and participating in a chat session that corresponds to the selected notification item.

The remote scribe device can generate and transmit a chat response (584). For example, an operator of the remote scribe device 106 can use the remote scribe interface 156 to generate the chat response, and the remote scribe device 106 can transmit the chat response to the server system 108. Referring again to FIG. 4G, for example, the interface 480 can present chat control 488 for the task-based chat thread for the imaging task for Patient F. The operator of the remote scribe device 106, for example, can review the chat thread including the communication data in the chat message provided by the practitioner interface device 102 (e.g., a recorded media file that includes the requested instructions, optionally transcribed by the server system 106). In the present example, after reviewing the chat thread presented in the chat control 488, Scribe E can provide input for a chat response (e.g., a short acknowledgement message, "Thanks!"), which is then transmitted to the server system 108.

The server system can receive and transmit the chat response (586). For example, the server system 108 can receive the chat response from the remote scribe device 106, and can transmit the chat response to the practitioner interface device 102 that is associated with the chat thread to which the chat response pertains. In the present example, the server system 108 can determine that the chat response pertains to the task-based chat thread for the imaging task for Patient F, and can transmit the chat response to the remote scribe device of Provider A3.

The practitioner interface device can receive the chat response (588), which can then present a chat notification (590). For example, the practitioner interface device 102 can receive the chat response, and in response can present a chat notification at the practitioner interface 152 of the practitioner interface device 102. Referring again to FIG. 6B, for example, screen 650 includes a chat notification icon (e.g., a visual icon in the upper-right hand corner of screen 650 or another suitable location), similar to chat notification icon 414 of the remote scribe interface 156. In response to a user interaction with the chat notification icon, for example, the practitioner interface 152 can present screen 670 (shown in FIG. 6C), which presents a list of multiple ongoing chat threads. Similar to the chat notification display 482 (shown in FIG. 4F) of the practitioner interface 152, for example, the list of chat threads can include indications of recently received unread chat messages (e.g., through bolded text, highlighting, animation, etc.). In the present example, the list item that corresponds to the task-based chat thread for the imaging task for Patient F can include an indication that an unread chat message exists in the chat thread.

The practitioner interface device can receive a chat dialog selection (592), and the practitioner interface device can present the chat response (594). For example, the practitioner interface device 102 can receive a chat dialog selection through the practitioner interface 152, and in response can present the response message content provided by the remote scribe device 106. In the present example, an operator of the practitioner interface device 102 (e.g., Provider A3) can select the list item that corresponds to the task-based chat thread for the imaging task for Patient F, and the practitioner interface 152 can be updated to present screen 680 (shown in FIG. 6C). As shown in screen 680, for example, the chat thread has been updated to include the acknowledgement message (e.g., "Thanks") provided by the operator of the remote scribe device 106 (e.g., Scribe E).

Figure 7:
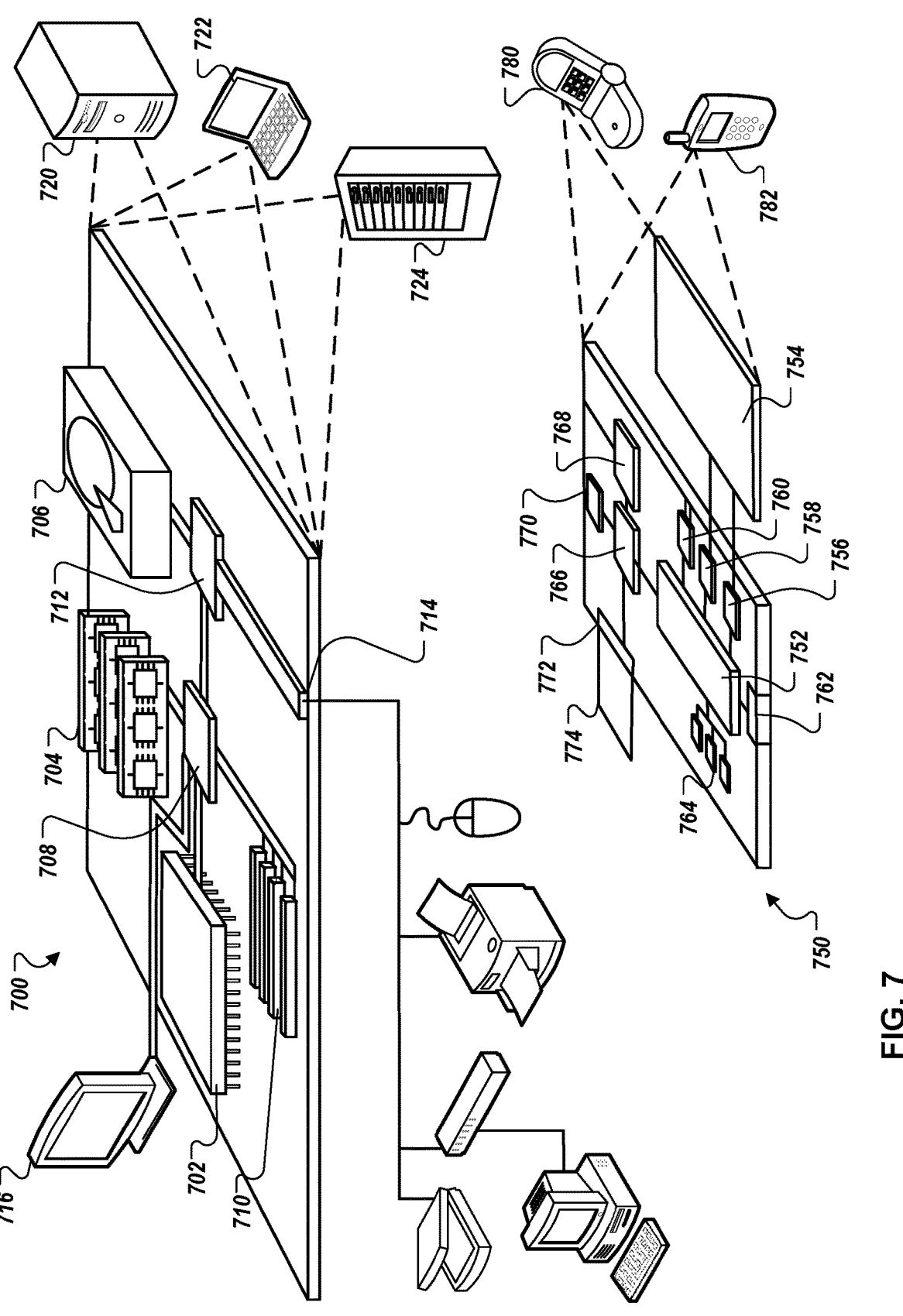
FIG. 7 is a schematic diagram that shows an example of a computing device and a mobile computing device.

FIG. 7 shows an example of a computing device 700 and an example of a mobile computing device 750 that can be used to implement the techniques described here. The computing device 700 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 700 includes a processor 702, a memory 704, a storage device 706, a high-speed interface 708 connecting to the memory 704 and multiple high-speed expansion ports 710, and a low-speed interface 712 connecting to a low-speed expansion port 714 and the storage device 706. Each of the processor 702, the memory 704, the storage device 706, the high-speed interface 708, the high-speed expansion ports 710, and the low-speed interface 712, are interconnected using various busses, and can be mounted on a common motherboard or in other manners as appropriate. The processor 702 can process instructions for execution within the computing device 700, including instructions stored in the memory 704 or on the storage device 706 to display graphical information for a GUI on an external input/output device, such as a display 716 coupled to the high-speed interface 708. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multiprocessor system).

The memory 704 stores information within the computing device 700. For example, the memory 704 is a volatile memory unit or units. For example, the memory 704 is a non-volatile memory unit or units. The memory 704 can also be another form of computer-readable medium, such as a magnetic or optical disk.

The storage device 706 is capable of providing mass storage for the computing device 700. For example, the storage device 706 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 704, the storage device 706, or memory on the processor 702.

The high-speed interface 708 manages bandwidth-intensive operations for the computing device 700, while the low-speed interface 712 manages lower bandwidth-intensive operations. Such allocation of functions is exemplary only. For example, the high-speed interface 708 is coupled to the memory 704, the display 716 (e.g., through a graphics processor or accelerator), and to the high-speed expansion ports 710, which can accept various expansion cards (not shown). In the implementation, the low-speed interface 712 is coupled to the storage device 706 and the low-speed expansion port 714. The low-speed expansion port 714, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 700 can be implemented in a number of different forms, as shown in the figure. For example, it can be implemented as a standard server 720, or multiple times in a group of such servers. In addition, it can be implemented in a personal computer such as a laptop computer 722. It can also be implemented as part of a rack server system 724. Alternatively, components from the computing device 700 can be combined with other components in a mobile device, such as mobile computing device 750. Each of such devices can contain one or more of the computing device 700 and the mobile computing device 750, and an entire system can be made up of multiple computing devices communicating with each other.

The mobile computing device 750 includes a processor 752, a memory 764, an input/output device such as a display 754, a communication interface 766, and a transceiver 768, among other components. The mobile computing device 750 can also be provided with a storage device, such as a micro-drive or other device, to provide additional storage. Each of the processor 752, the memory 764, the display 754, the communication interface 766, and the transceiver 768, are interconnected using various buses, and several of the components can be mounted on a common motherboard or in other manners as appropriate.

The processor 752 can execute instructions within the mobile computing device 750, including instructions stored in the memory 764. The processor 752 can be implemented as a chipset of chips that include separate and multiple analog and digital processors. The processor 752 can provide, for example, for coordination of the other components of the mobile computing device 750, such as control of user interfaces, applications run by the mobile computing device 750, and wireless communication by the mobile computing device 750.

The processor 752 can communicate with a user through a control interface 758 and a display interface 756 coupled to the display 754. The display 754 can be, for example, a TFT (Thin-Film-Transistor Liquid Crystal Display) display or an OLED (Organic Light Emitting Diode) display, or other appropriate display technology. The display interface 756 can comprise appropriate circuitry for driving the display 754 to present graphical and other information to a user. The control interface 758 can receive commands from a user and convert them for submission to the processor 752. In addition, an external interface 762 can provide communication with the processor 752, so as to enable near area communication of the mobile computing device 750 with other devices. The external interface 762 can provide, for example, for wired communication For example, or for wireless communication in other implementations, and multiple interfaces can also be used.

The memory 764 stores information within the mobile computing device 750. The memory 764 can be implemented as one or more of a computer-readable medium or media, a volatile memory unit or units, or a non-volatile memory unit or units. An expansion memory 774 can also be provided and connected to the mobile computing device 750 through an expansion interface 772, which can include, for example, a SIMM (Single In Line Memory Module) card interface. The expansion memory 774 can provide extra storage space for the mobile computing device 750, or can also store applications or other information for the mobile computing device 750. Specifically, the expansion memory 774 can include instructions to carry out or supplement the processes described above, and can include secure information also. Thus, for example, the expansion memory 774 can be provide as a security module for the mobile computing device 750, and can be programmed with instructions that permit secure use of the mobile computing device 750. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. For example, a computer program product is tangibly embodied in an information carrier. The computer program product contains instructions that, when executed, perform one or more methods, such as those described above. The computer program product can be a computer- or machine-readable medium, such as the memory 764, the expansion memory 774, or memory on the processor 752. For example, the computer program product can be received in a propagated signal, for example, over the transceiver 768 or the external interface 762.

The mobile computing device 750 can communicate wirelessly through the communication interface 766, which can include digital signal processing circuitry where necessary. The communication interface 766 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 768 using a radio-frequency. In addition, short-range communication can occur, such as using a Bluetooth, WiFi, or other such transceiver (not shown). In addition, a GPS (Global Positioning System) receiver module 770 can provide additional navigation- and location-related wireless data to the mobile computing device 750, which can be used as appropriate by applications running on the mobile computing device 750.

The mobile computing device 750 can also communicate audibly using an audio codec 760, which can receive spoken information from a user and convert it to usable digital information. The audio codec 760 can likewise generate audible sound for a user, such as through a speaker, e.g., in a handset of the mobile computing device 750. Such sound can include sound from voice telephone calls, can include recorded sound (e.g., voice messages, music files, etc.) and can also include sound generated by applications operating on the mobile computing device 750.

The mobile computing device 750 can be implemented in a number of different forms, as shown in the figure. For example, it can be implemented as a cellular telephone 780. It can also be implemented as part of a smart-phone 782, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

What is claimed is:

1. A computer-implemented method comprising:
    receiving, by a practitioner interface device, a command to record media data that pertains to a health care session that has been conducted between a health care provider and a patient;
    transmitting the media data, by the practitioner interface device and to a server system;
    receiving, by the practitioner interface device and from the server system, a media data receipt notification that indicates that the server system has received the media data;
    in response to receiving the media data receipt notification, automatically removing the media data from the practitioner interface device;
    after receiving the media data receipt notification, receiving, by the practitioner interface device and from the server system, at least one of (i) a process notification that indicates that a remote scribe device is currently processing a task that pertains to the health care session and the media data and (ii) an interference issue notification that indicates that the remote scribe device that is processing the task has flagged an interference issue that indicates a defect with the media data;
    after removing the media data from the practitioner interface device and after receiving at least one of the process notification and the interference issue notification, receiving, by the practitioner interface device and from the server system, a task completion notification that indicates that a task that pertains to the health care session and the media data has been completed;
    after receiving the task completion notification, updating a practitioner interface of the practitioner interface device to present one or more feedback controls for the completed task, the one or more feedback controls configured to receive input from an operator of the practitioner interface device; and
    providing, by the practitioner interface device and to the server system, non-patient-specific feedback data for the completed task, based on the input that has been received through the one or more feedback controls presented by the practitioner interface.

2. The computer-implemented method of claim 1, wherein the practitioner interface includes a plurality of selectable task controls, wherein each selectable task control represents a different task to be performed for the health care provider and includes a task status indicator that provides a visual indication of a current status of the task.

3. The computer-implemented method of claim 2, wherein the media data receipt notification further indicates that the server system has successfully stored the media data and the computer computer-implemented method further comprising:
    in response to receiving the media data receipt notification, updating the task status indicator of the selectable task control that represents the task that pertains to the health care session to indicate that the media data has been successfully uploaded and stored.

4. The computer-implemented method of claim 2, further comprising:

in response to receiving the process notification, updating the task status indicator of the selectable task control that represents the task that pertains to the health care session to indicate that the task is currently being processed by the remote scribe device.

5. The computer-implemented method of claim 2, further comprising:

in response to receiving the task completion notification, updating the task status indicator of the selectable task control that represents the task that pertains to the health care session to indicate that the task has been completed.

6. The computer-implemented method of claim 2, wherein updating the practitioner interface of the practitioner interface device to present one or more feedback controls for the completed task is performed in response to receiving a selection of the selectable task control that represents the completed task that pertains to the health care session.

7. The computer-implemented method of claim 2, further comprising:

in response to receiving the interference issue notification, updating the task status indicator of the selectable task control that represents the task that pertains to the health care session to indicate that the interference issue exists for the task.

8. The computer-implemented method of claim 7, further comprising:

receiving a selection of the selectable task control that represents the task that pertains to the health care session and for which the interference issue exists;

in response to receiving the selection of the selectable task control, updating the practitioner interface of the practitioner interface device to present one or more controls for providing additional task data for correcting the interference issue; and providing, by the practitioner interface device and to the server system, the additional task data, based on input that has been received through the one or more controls for providing the additional task data.

9. A computer-implemented method comprising:

receiving, by a practitioner interface device, a command to record media data that pertains to a health care session that has been conducted between a health care provider and a patient;

transmitting the media data, by the practitioner interface device and to a server system;

receiving, by the practitioner interface device and from the server system, a media data receipt notification that indicates that the server system has received the media data;

in response to receiving the media data receipt notification, automatically removing the media data from the practitioner interface device;

after receiving the media data receipt notification, receiving, by the practitioner interface device and from the server system, at least one of (i) a process notification that indicates that a remote scribe device is currently processing a task that pertains to the health care session and the media data and (ii) an interference issue notification that indicates that the remote scribe device that is processing the task has flagged an interference issue that indicates a defect with the media data;

after removing the media data from the practitioner interface device and after receiving at least one of the process notification and the interference issue notification, receiving, by the practitioner interface device and from the server system, a task completion notification that indicates that a task that pertains to the health care session and the media data has been completed;

after receiving the task completion notification, updating a practitioner interface of the practitioner interface device to present one or more feedback controls for the completed task, the one or more feedback controls configured to receive input from an operator of the practitioner interface device;

providing, by the practitioner interface device and to the server system, non-patient-specific feedback data for the completed task, based on the input that has been received through the one or more feedback controls presented by the practitioner interface; and in response to a selection of a chat control of the practitioner interface of the practitioner interface device, updating the practitioner interface to present a plurality of selectable chat thread controls, wherein each selectable chat thread control represents an ongoing chat thread between the practitioner interface device and one or more remote scribe devices.

10. The computer-implemented method of claim 9, wherein at least one of the selectable chat thread controls represents the ongoing chat thread between the practitioner interface device and a remote scribe device that is processing the task that pertains to the health care session and the media data.

11. A computer system comprising:

one or more computers; and one or more computer memory devices interoperably coupled with the one or more computers and having tangible, non-transitory, machine-readable media storing one or more instructions that, when executed by the one or more computers, perform one or more operations comprising:

receiving, by a practitioner interface device, a command to record media data that pertains to a health care session that has been conducted between a health care provider and a patient;

transmitting the media data, by the practitioner interface device and to a server system;

receiving, by the practitioner interface device and from the server system, a media data receipt notification that indicates that the server system has received the media data;

in response to receiving the media data receipt notification, automatically removing the media data from the practitioner interface device;

after receiving the media data receipt notification, receiving, by the practitioner interface device and from the server system, at least one of (i) a process notification that indicates that a remote scribe device is currently processing a task that pertains to the health care session and the media data and (ii) an interference issue notification that indicates that the remote scribe device that is processing the task has flagged an interference issue that indicates a defect with the media data;

after removing the media data from the practitioner interface device and after receiving at least one of the process notification and the interference issue notification, receiving, by the practitioner interface device and from the server system, a task completion notification that indicates that a task that pertains to the health care session and the media data has been completed;

after receiving the task completion notification, updating a practitioner interface of the practitioner interface device to present one or more feedback controls for the completed task, the one or more feedback controls configured to receive input from an operator of the practitioner interface device; and providing, by the practitioner interface device and to the server system, non-patient-specific feedback data for the completed task, based on the input that has been received through the one or more feedback controls presented by the practitioner interface.

12. The computer system of claim 11, wherein the practitioner interface includes a plurality of selectable task controls, wherein each selectable task control represents a different task to be performed for the health care provider and includes a task status indicator that provides a visual indication of a current status of the task.

13. The computer system of claim 12, the operations further comprising:

in response to receiving the media data receipt notification, updating the task status indicator of the selectable task control that represents the task that pertains to the health care session to indicate that the media data has been uploaded.

14. The computer system of claim 12, the operations further comprising:

in response to receiving the process notification, updating the task status indicator of the selectable task control that represents the task that pertains to the health care session to indicate that the task is currently being processed by the remote scribe device.

15. The computer system of claim 12, the operations further comprising:

in response to receiving the task completion notification, updating the task status indicator of the selectable task control that represents the task that pertains to the health care session to indicate that the task has been completed.

16. The computer system of claim 12, wherein updating the practitioner interface of the practitioner interface device to present one or more feedback controls for the completed task is performed in response to receiving a selection of the selectable task control that represents the completed task that pertains to the health care session.

17. The computer system of claim 12, the operations further comprising:

in response to receiving the interference issue notification, updating the task status indicator of the selectable task control that represents the task that pertains to the health care session to indicate that the interference issue exists for the task.

18. The computer system of claim 17, the operations further comprising:

receiving a selection of the selectable task control that represents the task that pertains to the health care session and for which the interference issue exists;

in response to receiving the selection of the selectable task control, updating the practitioner interface of the practitioner interface device to present one or more controls for providing additional task data for correcting the interference issue; and providing, by the practitioner interface device and to the server system, the additional task data, based on input that has been received through the one or more controls for providing the additional task data.

19. The computer system of claim 11, the operations further comprising:

in response to a selection of a chat control of the practitioner interface of the practitioner interface device, updating the practitioner interface to present a plurality of selectable chat thread controls, wherein each selectable chat thread control represents an ongoing chat thread between the practitioner interface device and one or more remote scribe devices.

20. The computer system of claim 19, wherein at least one of the selectable chat thread controls represents the ongoing chat thread between the practitioner interface device and the remote scribe device that is processing the task that pertains to the health care session and the media data.

* * * * *